(12) United States Patent
Chen et al.

(10) Patent No.: US 7,494,983 B2
(45) Date of Patent: Feb. 24, 2009

(54) OPHTHALMIC COMPOSITIONS FOR TREATING OCULAR HYPERTENSION

(75) Inventors: Meng Hsin Chen, Westfield, NJ (US); James B. Doherty, Montvale, NJ (US); Luping Liu, Plainsboro, NJ (US); Swaminathan Natarajan, Scotch Plains, NJ (US); Robert M. Tynebor, Woodbridge, NJ (US)

(73) Assignee: Merck & Co. Inc., Rahway, NJ (US)

( * ) Notice: Subject to any disclaimer, the term of this patent is extended or adjusted under 35 U.S.C. 154(b) by 328 days.

(21) Appl. No.: 10/570,231

(22) PCT Filed: Aug. 31, 2004

(86) PCT No.: PCT/US2004/028351

§ 371 (c)(1),
(2), (4) Date: Feb. 28, 2006

(87) PCT Pub. No.: WO2005/255568

PCT Pub. Date: Mar. 24, 2005

(65) Prior Publication Data

US 2007/0027188 A1    Feb. 1, 2007

Related U.S. Application Data

(60) Provisional application No. 60/500,090, filed on Sep. 4, 2003.

(51) Int. Cl.
*A61K 31/675* (2006.01)
*A61K 31/4439* (2006.01)
*C07F 9/06* (2006.01)

(52) U.S. Cl. .............. 514/80; 514/89; 514/338; 514/406; 546/22; 546/24; 548/113

(58) Field of Classification Search .............. 514/80, 514/89, 338, 406; 546/22, 24; 548/113
See application file for complete search history.

(56) References Cited

U.S. PATENT DOCUMENTS

| 4,690,931 A | 9/1987 | Wick et al. |
| 5,151,444 A | 9/1992 | Ueno et al. |
| 5,296,504 A | 3/1994 | Stjernschantz et al. |
| 5,352,708 A | 10/1994 | Woodward et al. |
| 5,422,368 A | 6/1995 | Stjernschantz et al. |
| 5,573,758 A | 11/1996 | Adorante et al. |
| 5,889,052 A | 3/1999 | Klimko et al. |
| 5,925,342 A | 7/1999 | Adorante et al. |

FOREIGN PATENT DOCUMENTS

| EP | 1114816 | 7/2001 |
| WO | WO 89/10757 | 11/1989 |
| WO | WO 94/13275 | 6/1994 |
| WO | WO 94/28900 | 12/1994 |
| WO | WO 96/33719 | 10/1996 |
| WO | WO 01/70702 | 9/2001 |
| WO | WO 01/72268 A1 | 10/2001 |
| WO | WO 02/24647 | 3/2002 |
| WO | WO 02/42268 | 5/2002 |
| WO | WO 01/46140 | 6/2004 |
| WO | WO 2004/085431 | 10/2004 |

OTHER PUBLICATIONS

Wiederholt et al. (Progress in Retinal & Eye Research 2000, 19(3), 271-295).*
A. M. Harman et al., "Development and Aging of Cell Topography in the Human Retinal Pigment Epithelium", 1997, pp. 2016-2026, vol. 38, No. 10, Investigative Ophthalmology & Visual Science.
E. L. Eliel et al., "Chirality in Molecules Devoid of Chiral Centers", 1994, pp. 1119-1190, Chap. 14, *Stereochemistry of Organic Compounds*.
S. M. Berge et al., "Pharmaceutical Salts", 1977, pp. 1-19, vol. 66, No. 1, J. of Pharmaceutical Sciences.
H. Eto et al., "New Antifungal 1,2,4-Triazoles with Difluoro (heteroaryl) methyl Moiety", 2000, pp. 982-990, vol. 48, No. 7, Chem. Pharm. Bull.
O. P. Hamill et al., "Improved Patch Claim Techniques for High-Resolution Current Recording from Cells and Cell-Free Membrane Patches", 1981, pp. 82-100, vol. 391, Pflugers Archiv.

* cited by examiner

*Primary Examiner*—Kamal A Saeed
*Assistant Examiner*—Jason Nolan
(74) *Attorney, Agent, or Firm*—Sylvia A. Ayler; William Krovatin

(57) ABSTRACT

This invention relates to potent potassium channel blocker compounds of structural Formula I or a formulation thereof for the treatment of glaucoma and other conditions which leads to elevated intraoccular pressure in the eye of a patient. This invention also relates to the use of such compounds to provide a neuroprotective effect to the eye of mammalian species, particularly humans.

14 Claims, No Drawings

OPHTHALMIC COMPOSITIONS FOR TREATING OCULAR HYPERTENSION

This application claims the benefit under 35 U.S.C. 119(e) of U.S. Provisional Application No. 60/500,090 filed Sep. 4, 2003.

BACKGROUND OF THE INVENTION

Glaucoma is a degenerative disease of the eye wherein the intraocular pressure is too high to permit normal eye function. As a result, damage may occur to the optic nerve head and result in irreversible loss of visual function. If untreated, glaucoma may eventually lead to blindness. Ocular hypertension, i.e., the condition of elevated intraocular pressure without optic nerve head damage or characteristic glaucomatous visual field defects, is now believed by the majority of ophthalmologists to represent merely the earliest phase in the onset of glaucoma.

There are several therapies for treating glaucoma and elevated intraocular pressure, but the efficacy and the side effect profiles of these agents are not ideal. Recently potassium channel blockers were found to reduce intraocular pressure in the eye and therefore provide yet one more approach to the treatment of ocular hypertension and the degenerative ocular conditions related thereto. Blockage of potassium channels can diminish fluid secretion, and under some circumstances, increase smooth muscle contraction and would be expected to lower IOP and have neuroprotective effects in the eye. (see U.S. Pat. Nos. 5,573,758 and 5,925,342; Moore, et al., Invest. Ophthalmol. Vis. Sci 38, 1997; WO 89/10757, WO94/28900, and WO 96/33719).

SUMMARY OF THE INVENTION

This invention relates to the use of potent potassium channel blockers or a formulation thereof in the treatment of glaucoma and other conditions which are related to elevated intraocular pressure in the eye of a patient. This invention also relates to the use of such compounds to provide a neuroprotective effect to the eye of mammalian species, particularly humans. More particularly this invention relates to the treatment of glaucoma and/or ocular hypertension (elevated intraocular pressure) using novel phosphate containing indazole compounds having the structural formula I:

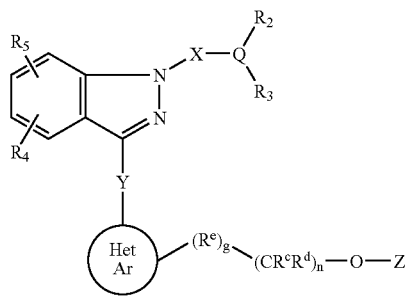

Formula I or a pharmaceutically acceptable salt, in vivo hydrolysable ester, enantiomer, diastereomer or mixture thereof:

wherein,

R represents hydrogen, or $C_{1-6}$ alkyl;

$R^c$ and $R^d$ independently represents hydrogen or halo;

$R^e$ represents N or O;

X represents $-(CHR_7)_p-$, $-(CHR_7)_pCO-$;

Y represents $-CO(CH_2)_n-$, $CH_2$, or $-CH(OR)-$;

Q represents N, or O, wherein $R_2$ is absent when Q is O;

$R_w$ represents H, $C_{1-6}$ alkyl, $-C(O)C_{1-6}$ alkyl, $-C(O)OC_{1-6}$ alkyl, $-SO_2N(R)_2$, $-SO_2C_{1-6}$ alkyl, $-SO_2C_{6-10}$ aryl, $NO_2$, CN or $-C(O)N(R)_2$;

$R_2$ represents hydrogen, $C_{1-10}$ alkyl, OH, $C_{2-6}$ alkenyl, $C_{1-6}$ alkylSR, $-(CH_2)_nO(CH_2)_mOR$, $-(CH_2)_nC_{1-6}$-alkoxy, $-(CH_2)_nC_{3-8}$ cycloalkyl, $-(CH_2)_nC_{3-10}$ heterocyclyl, $-N(R)_2$, $-COOR$, or $-(CH_2)_nC_{6-10}$ aryl, said alkyl, heterocyclyl, or aryl optionally substituted with 1-3 groups selected from $R^a$;

$R_3$ represents hydrogen, $C_{1-10}$ alkyl, $-(CH_2)_nC_{3-8}$ cycloalkyl, $-(CH_2)_nC_{3-10}$ heterocyclyl, $-(CH_2)_nCOOR$, $-(CH_2)_nC_{6-10}$ aryl, $-(CH_2)_nNHR_8$, $-(CH_2)_nN(R)_2$, $-(CH_2)_nN(R_8)_2$, $-(CH_2)_nNHCOOR$, $-(CH_2)_nN(R_8)CO_2R$, $-(CH_2)_nN(R_8)COR$, $-(CH_2)_nNHCOR$, $-(CH_2)_nCONH(R_8)$, aryl, $-(CH_2)_nC_{1-6}$ alkoxy, $CF_3$, $-(CH_2)_nSO_2R$, $-(CH_2)_nSO_2N(R)_2$, $-(CH_2)_nCON(R)_2$, $-(CH_2)_nCONHC(R)_3$, $-(CH_2)_nCONHC(R)_2CO_2R$, $-(CH_2)_nCOR_8$, nitro, cyano or halogen, said alkyl, alkoxy, heterocyclyl, or aryl optionally substituted with 1-3 groups of $R^a$;

or, $R_2$ and $R_3$ taken together with the intervening Q form a 3-10 membered carbocyclic or heterocyclic carbon ring optionally interrupted by 1-2 atoms of O, S, C(O) or NR, and optionally having 1-4 double bonds, and optionally substituted by 1-3 groups selected from $R^a$;

$R_4$ and $R_5$ independently represent hydrogen, $C_{1-6}$ alkoxy, OH, $C_{1-6}$ alkyl, COOR, $SO_3H$, $-O(CH_2)_nN(R)_2$, $-O(CH_2)_nCO_2R$, $-OPO(OH)_2$, $CF_3$, $OCF_3$, $-N(R)_2$, nitro, cyano, $C_{1-6}$ alkylamino, or halogen;

represents $C_{6-10}$ aryl or $C_{3-10}$ heterocyclyl, said aryl or heterocyclyl optionally substituted with 1-3 groups selected from $R^a$;

Z represents $(CH_2)_nPO(OR)(OR^*)$;

$R^*$ represents hydrogen, or $C_{1-6}$ alkyl;

$R_7$ represents hydrogen, $C_{1-6}$ alkyl, $-(CH_2)_nCOOR$ or $-(CH_2)_nN(R)_2$, $R_8$ represents $-(CH_2)_nC_{3-8}$ cycloalkyl, $-(CH_2)_n$ 3-10 heterocyclyl, $C_{1-6}$ alkoxy or $-(CH_2)_nC_{5-10}$ heteroaryl, $-(CH_2)_nC_{6-10}$ aryl said heterocyclyl, aryl or heteroaryl optionally substituted with 1-3 groups selected from $R^a$;

$R^a$ represents F, Cl, Br, I, $CF_3$, $N(R)_2$, $NO_2$, CN, $-COR_8$, $-CONHR_8$, $-CON(R_8)_2$, $-O(CH_2)_nCOOR$, $-NH(CH_2)_nOR$, $-COOR$, $-OCF_3$, $-NHCOR$, $-SO_2R$, $-SO_2NR_2$, $-SR$, $(C_1-C_6$ alkyl)$O-$, $-(CH_2)_nO(CH_2)_mOR$, $-(CH_2)_nC_{1-6}$ alkoxy, (aryl)$O-$, $-(CH_2)_nOH$, $(C_1-C_6$ alkyl)$S(O)_m-$, $H_2N-C(NH)-$, $(C_1-C_6$ alkyl)$C(O)-$, $(C_1-C_6$ alkyl)$OC(O)NH-$, $-(C_1-C_6$ alkyl)$NR_w(CH_2)_nC_{3-10}$ heterocyclyl-$R_w$, $-(C_1-C_6$ alkyl)$O(CH_2)_nC_{3-10}$ heterocyclyl-$R_w$, $-(C_1-C_6$ alkyl)$S(CH_2)_nC_{3-10}$ heterocyclyl-$R_w$, $-(C_1-C_6$ alkyl)$-C_{3-10}$ heterocyclyl-$R_w$, $-(CH_2)_n$-$Z^1$-$C(=Z^2)N(R)_2$, $-(C_{2-6}$ alkenyl)$NR_w(CH_2)_nC_{3-10}$ heterocyclyl-$R_w$, $-(C_{2-6}$ alkenyl)$O(CH_2)_nC_{3-10}$ heterocyclyl-$R_w$, $-(C_{2-6}$ alkenyl)$S(CH_2)_nC_{3-10}$ heterocyclyl-$R_w$, $-(C_{2-6}$ alkenyl)-$C_{3-10}$ heterocyclyl-$R_w$, $-(C_{2-6}$ alkenyl)-$Z^1$-$C(=Z^2)N(R)_2$, $-(CH_2)_nSO_2R$, $-(CH_2)_nSO_3H$, $-(CH_2)_nPO(OR)_2$, $C_{3-10}$cycloalkyl, $C_{6-10}$ aryl, $C_{3-10}$ heterocyclyl, $C_{2-6}$ alkenyl, and $C_1$-$C_{10}$ alkyl, said alkyl, alkenyl, alkoxy, heterocyclyl and aryl optionally substituted with 1-3 groups selected from $C_1$-$C_6$ alkyl, CN, $NO_2$, OH, $CON(R)_2$ and COOR;

$Z^1$ and $Z^2$ independently represents $NR_w$, O, $CH_2$, or S;

g is 0-1;
m is 0-3;
n is 0-3; and
p is 0-3.

This and other aspects of the invention will be realized upon inspection of the invention as a whole.

DETAILED DESCRIPTION OF THE INVENTION

The present invention is directed to novel potassium channel blockers of Formula I. It also relates to a method for decreasing elevated intraocular pressure or treating glaucoma by administration, preferably topical or intra-camaral administration, of a composition containing a potassium channel blocker of Formula I described hereinabove and a pharmaceutically acceptable carrier. This invention is also concerned with the use of a compound of formula I for the manufacture of a medicament for the treatment of ocular hypertension or glaucoma.

In an embodiment of the instant compounds are those compounds where p is 1-3.

One embodiment of this invention is realized when Q is N and all other variables are as originally described.

Another embodiment of this invention is realized when Q is O and $R_2$ is absent and all other variables are as originally described.

Another embodiment of this invention is realized when Y is —$CO(CH_2)_n$— and all other variables are as originally described. A subembodiment of this invention is realized when n is 0.

Another embodiment of this invention is realized when Y is CH(OR) and all other variables are as originally described.

Another embodiment of this invention is realized when Z is PO(OR)(OR*) and R and R* are H. A sub-embodiment of this invention is realized when R and R* are $C_{1-6}$ alkyl.

In another embodiment $R_w$ is selected from H, $C_{1-6}$ alkyl, —$C(O)C_{1-6}$ alkyl and —$C(O)N(R)_2$ and all other variables are as originally described.

In another embodiment X is —$(CHR_7)_p$—, p is 1-3 and all other variables are as originally described.

In another embodiment X is —$(CHR_7)_pCO$—, p is 1-3 and all other variables are as originally described.

In another embodiment $$\text{Het Ar}$$

is a 6 membered heteroaryl or phenyl optionally substituted with 1-3 groups selected from $R^a$. A subembodiment of this invention is realized when the heteroaryl is pyridyl.

Yet another embodiment of this invention is realized when $R_7$ is hydrogen or $C_{1-6}$ alkyl, and all other variables are as originally described.

Still another embodiment of this invention is realized when Z is PO(OR)(OR*), $R_2$ and and $R_3$ independently are hydrogen, $C_{1-10}$ alkyl or $C_{1-6}$alkylOH, and Y is —$CO(CH_2)_n$ Another embodiment of the instant invention is realized when $R^a$ is selected from F, Cl, Br, I, $CF_3$, $N(R)_2$, $NO_2$, CN, —$CONHR_8$, —$CON(R_8)_2$, —$O(CH_2)_nCOOR$, —$NH(CH_2)_n$ OR, —COOR, —$OCF_3$, —NHCOR, —$SO_2R$, —$SO_2NR_2$, —SR, $(C_1$-$C_6$ alkyl)O—, —$(CH_2)_nO(CH_2)_mOR$, —$(CH_2)_n$ $C_{1-6}$ alkoxy, (aryl)O—, —$(CH_2)_nOH$, $(C_1$-$C_6$ alkyl)S(O)$_m$—, $H_2N$—C(NH)—, $(C_1$-$C_6$ alkyl)C(O)—, —$(CH_2)_nPO(OR)_2$, $C_{2-6}$ alkenyl, and $C_1$-$C_{10}$ allyl, said alkyl and alkenyl, optionally substituted with 1-3 groups selected from $C_1$-$C_6$ alkyl, and COOR.

Examples of compounds of structural formula I are found in Table 1:

TABLE 1

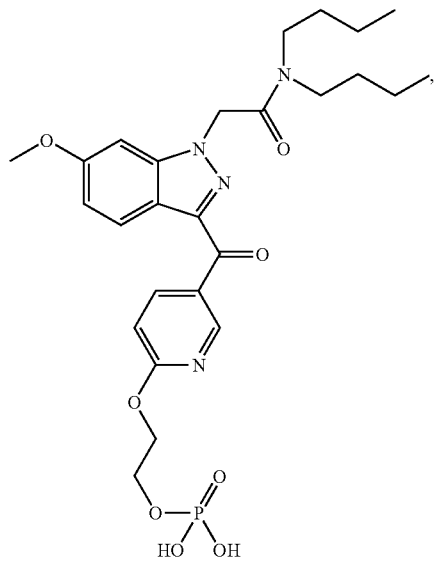

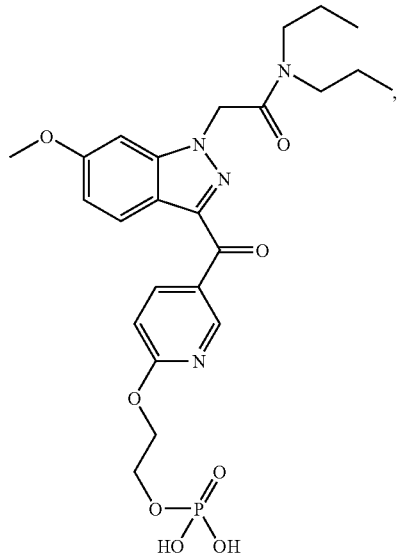

TABLE 1-continued

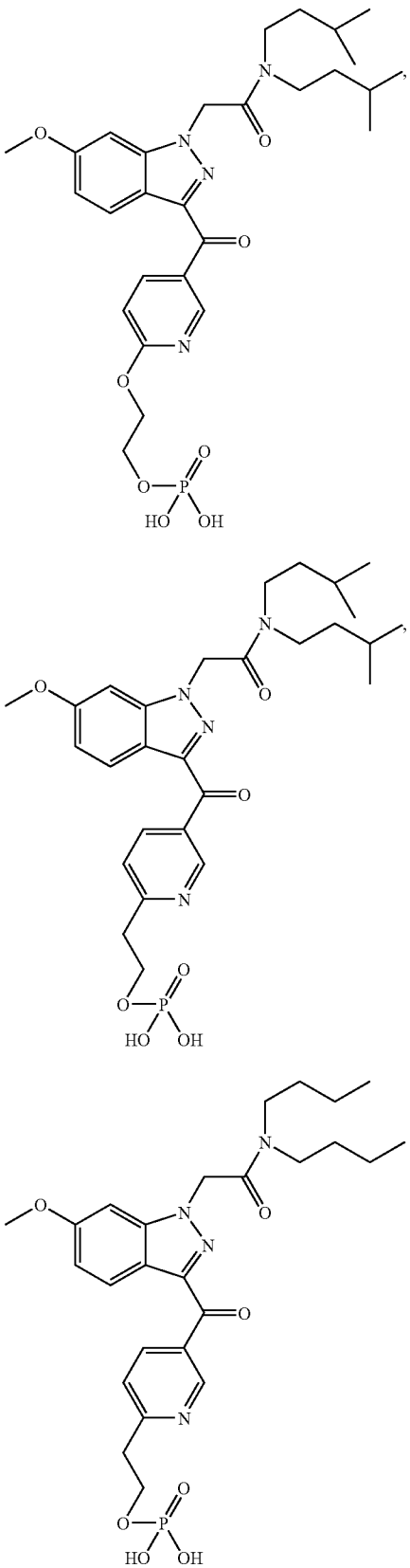

or a pharmaceutically acceptable salt, enantiomer, diastereomer or mixture thereof. A sub-embodiment of this invention is realized when the compounds are in the form of a monosodium or disodium salt.

The invention is described herein in detail using the terms defined below unless otherwise specified.

The compounds of the present invention may have asymmetric centers, chiral axes and chiral planes, and occur as racemates, racemic mixtures, and as individual diastereomers, with all possible isomers, including optical isomers, being included in the present invention. (See E. L. Eliel and S. H. Wilen *Stereochemistry of Carbon Compounds* (John Wiley and Sons, New York 1994), in particular pages 1119-1190).

When any variable (e.g. aryl, heterocycle, $R^1$, $R^6$ etc.) occurs more than one time in any constituent, its definition on each occurrence is independent at every other occurrence. Also, combinations of substituents/or variables are permissible only if such combinations result in stable compounds.

The term "alkyl" refers to a monovalent alkane (hydrocarbon) derived radical containing from 1 to 10 carbon atoms unless otherwise defined. It may be straight, branched or cyclic. Preferred alkyl groups include methyl, ethyl, propyl, isopropyl, butyl, t-butyl, cyclopropyl cyclopentyl and cyclohexyl. When the alkyl group is said to be substituted with an alkyl group, this is used interchangeably with "branched alkyl group".

Cycloalkyl is a specie of alkyl containing from 3 to 15 carbon atoms, unless otherwise defined, without alternating or resonating double bonds between carbon atoms. It may contain from 1 to 4 rings, which are fused. Examples of such cycloalkyl elements include, but are not limited to, cyclopropyl, cyclobutyl, cyclopentyl, cyclohexyl and cycloheptyl.

Alkenyl is $C_2$-$C_6$ alkenyl.

Alkoxy refers to an alkyl group of indicated number of carbon atoms attached through an oxygen bridge, with the alkyl group optionally substituted as described herein. Said groups are those groups of the designated length in either a straight or branched configuration and if two or more carbon atoms in length, they may include a double or a triple bond. Exemplary of such alkoxy groups are methoxy, ethoxy, propoxy, isopropoxy, butoxy, isobutoxy, tertiary butoxy, pentoxy, isopentoxy, hexoxy, isohexoxy allyloxy, propargyloxy, and the like.

Halogen (halo) refers to chlorine, fluorine, iodine or bromine.

Aryl refers to aromatic rings e.g., phenyl, substituted phenyl and the like, as well as rings which are fused, e.g., naphthyl, phenanthrenyl and the like. An aryl group thus contains at least one ring having at least 6 atoms, with up to five such rings being present, containing up to 22 atoms therein, with alternating (resonating) double bonds between adjacent carbon atoms or suitable heteroatoms. Examples of aryl groups are phenyl, naphthyl, tetrahydronaphthyl, indanyl, biphenyl, phenanthryl, anthryl or acenaphthyl and phenanthrenyl, preferably phenyl, naphthyl or phenanthrenyl. Aryl groups may likewise be substituted as defined. Preferred substituted aryls include phenyl and naphthyl.

The term heterocyclyl or heterocyclic, as used herein, represents a stable 3- to 7-membered monocyclic or stable 8- to 11-membered bicyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. A fused heterocyclic ring system may include carbocyclic rings and need include only one heterocyclic ring. The term heterocycle or heterocyclic includes heteroaryl moieties. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, dihydropyrrolyl, 1,3-dioxolanyl, furyl, imidazolidinyl, imidazolinyl, imidazolyl, indolinyl, indolyl, isochrroaanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperdinyl, 2-oxopyrrolidinyl, piperidyl, piperazinyl, pyridyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, and thienyl. Preferably, heterocycle is selected from 2-azepinonyl, benziridazolyl, 2-diazapinonyl, dihydroimidazolyl, dihydropyrrolyl, imidazolyl, 2-imidazolidinonyl, indolyl, isoquinolinyl, morpholinyl, piperidyl, piperazinyl, pyridyl, pyrrolidinyl, 2-piperidinonyl, 2-pyrimidinonyl, 2-pyrollidinonyl, quinolinyl, tetrahydrofuryl, tetrahydroisoquinolinyl, and thienyl.

The term "heteroatom" means O, S or N, selected on an independent basis.

The term "heteroaryl" refers to a monocyclic aromatic hydrocarbon group having 5 or 6 ring atoms, or a bicyclic aromatic group having 8 to 10 atoms, containing at least one heteroatom, O, S or N, in which a carbon or nitrogen atom is the point of attachment, and in which one or two additional carbon atoms is optionally replaced by a heteroatom selected from O or S, and in which from 1 to 3 additional carbon atoms are optionally replaced by nitrogen heteroatoms, said heteroaryl group being optionally substituted as described herein. Examples of such heterocyclic elements include, but are not limited to, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dibydrobenzothienyl, dihydrobenzothiopyranyl, dihydrobenzothiopyranyl sulfone, furyl, imidazolyl, indolinyl, indolyl, isochromanyl, isoindolinyl, isoquinolinyl, isothiazolyl, naphthyridinyl, oxadiazolyl, pyridyl, pyrazinyl, pyrazolyl, pyridazinyl, pyrinudinyl, pyrrolyl, quinazolinyl, quinolinyl, quinoxalinyl, tetrahydroisoquinolinyl, tetrahydroquinolinyl, thiazolyl, thienofuryl, thienothienyl, thienyl and triazolyl. Additional nitrogen atoms may be present together with the first nitrogen and oxygen or sulfur, giving, e.g., thiadiazole.

This invention is also concerned with compositions and methods of treating ocular hypertension or glaucoma by administering to a patient in need thereof one of the compounds of formula I alone or in combination with one or more of the following active ingredients, in combination with a β-adrenergic blocking agent such as timolol, betaxolol, levobetaxolol, carteolol, levobunolol, a parasympathomimetic agent such as epinephrine, iopidine, brimonidine, clonidine, para-aminoclonidine, carbonic anhydrase inhibitor such as dorzolamide, acetazolamide, metazolamide or brinzolamide, an EP4 agonist (such as those disclosed in WO 02124647, WO 02/42268, EP 1114816, WO 01/46140, PCT Appln. No. CA2004000471, and WO 01/72268), a prostaglandin such as latanoprost, travaprost, unoprostone, rescula, S1033 (compounds set forth in U.S. Pat. Nos. 5,889,052; 5,296,504; 5,422,368; and 5,151,444); a hypotensive lipid such as lumigan and the compounds set forth in U.S. Pat. No. 5,352,708; a neuroprotectant disclosed in U.S. Pat. No. 4,690,931, particularly eliprodil and R-eliprodil as set forth in WO 94/13275, including memantine; an agonist of 5-HT2 receptors as set forth in PCT/US00/31247, particularly 1-(2-aminopropyl)-3-methyl-1H-imdazol-6-ol fumarate and 2-(3-chloro-6-methoxy-indazol-1-yl)-1-methyl-ethylamine or a mixture thereof. An example of a hypotensive lipid (the carboxylic acid group on the α-chain link of the basic prostaglandin structure is replaced with electrochemically neutral substituents) is that in which the carboxylic acid group is replaced with a $C_{1-6}$ alkoxy group such as $OCH_3$ ($PGF_{2\alpha}$ 1-$OCH_3$), or a hydroxy group ($PGF_{2\alpha}$ 1-OH).

Preferred potassium channel blockers are calcium activated potassium channel blockers. More preferred potassium channel blockers are high conductance, calcium activated potassium (Maxi-K) channel blockers. Maxi-K channels are a family of ion channels that are prevalent in neuronal, smooth muscle and epithelial tissues and which are gated by membrane potential and intracellular $Ca^{2+}$.

The present invention is based upon the finding that maxi-K channels, if blocked, inhibit aqueous humor production by inhibiting net solute and $H_2O$ efflux and therefore lower IOP. This finding suggests that maxi-K channel blockers are useful for treating other ophthamological dysfunctions such as macular edema and macular degeneration. It is known that lowering IOP promotes blood flow to the retina and optic nerve. Accordingly, the compounds of this invention are useful for treating macular edema and/or macular degeneration. This invention also relates to the use of a compound of formula I for the manufacture of a medicament for the treatment of macular edema and/or macular degeneration.

It is believed that maxi-K channel blockers which lower IOP are useful for providing a neuroprotective effect. They are also believed to be effective for increasing retinal and optic nerve head blood velocity and increasing retinal and optic nerve oxygen by lowering IOP, which when coupled together benefits optic nerve health. As a result, this invention further relates to a method for increasing retinal and optic nerve head blood velocity, increasing retinal and optic nerve oxygen tension as well as providing a neuroprotective effect or a combination thereof. This invention also relates to the use of a compound of formula I for the manufacture of a medicament for the treatment of these diseases.

A number of marketed drugs function as potassium channel antagonists. The most important of these include the compounds Glyburide, Glipizide and Tolbutaride. These potassium channel antagonists are useful as antidiabetic agents. The compounds of this invention may be combined with one or more of these compounds to treat diabetes.

Potassium channel antagonists are also utilized as Class 3 antiarrhythmic agents and to treat acute infarctions in humans. A number of naturally occuring toxins are known to block potassium channels including Apamin, Iberiotoxin, Charybdotoxin, Noxiustoxin, Kaliotoxin, Dendrotoxin(s), mast cell degranuating (MCD) peptide, and β-Bungarotoxin (β-BTX). The compounds of this invention may be combined with one or more of these compounds to treat arrhythmias. This invention also relates to the use of a compound of formula I for the manufacture of a medicament for the treatment of arrhythmias.

Depression is related to a decrease in neurotransmitter release. Current treatments of depression include blockers of neurotransmitter uptake, and inhibitors of enzymes involved in neurotransmitter degradation which act to prolong the lifetime of neurotransmitters.

Alzheimer's disease is also characterized by a diminished neurotransmitter release. Three classes of drugs are being investigated for the treatment of Alzheimer's disease cholinergic potentiators such as the anticholinesterase drugs (e.g., physostigmine (eserine), and Tacrine (tetrahydroaminocridine)); nootropics that affect neuron metabolism with little effect elsewhere (e.g., Piracetam, Oxiracetam; and those drugs that affect brain vasculature such as a mixture of ergoloid mesylates amd calcium channel blocking drugs including Nimodipine. Selegiline, a monoamine oxidase B inhibitor which increases brain dopamine and norepinephrine has reportedly caused mild improvement in some Alzheimer's patients. Aluminum chelating agents have been of interest to those who believe Alzheimer's disease is due to aluminum toxicity. Drugs that affect behavior, including neuroleptics, and anxiolytics have been employed. Anxiolytics, which are mild tranquilizers, are less effective than neuroleptics The present invention is related to novel compounds which are useful as potassium channel antagonists. This invention also relates to the use of a compound of formula I for the manufacture of a medicament for the treatment of depression and/or Alzeheimer's disease.

The compounds of this invention may be combined with anticholinesterase drugs such as physostigmine (eserine) and Tacrine (tetrahydroaminocridine), nootropics such as Piracetam, Oxiracetam, ergoloid mesylates, selective calcium channel blockers such as Nimodipine, or monoamine oxidase B inhibitors such as Selegiline, in the treatment of Alzheimer's disease. The compounds of this invention may also be combined with Apamnin, Iberiotoxin, Charybdotoxin, Noxiustoxin, Kaliotoxin, Dendrotoxin(s), mast cell degranuating (MCD) peptide, $\beta$-Bungarotoxin ($\beta$-BTX) or a combination thereof in treating arrythmias. The compounds of this invention may further be combined with Glyburide, Glipizide, Tolbutamide or a combination thereof to treat diabetes. This invention also relates to the use of a compound of formula I for the manufacture of a medicament for the treatment of diabetes.

The herein examples illustrate but do not limit the claimed invention. Each of the claimed compounds are potassium channel antagonists and are thus useful in the described neurological disorders in which it is desirable to maintain the cell in a depolarized state to achieve maximal neurotransmitter release. The compounds produced in the present invention are readily combined with suitable and known pharmaceutically acceptable excipients to produce compositions which may be administered to mammals, including humans, to achieve effective potassium channel blockage.

For use in medicine, the salts of the compounds of formula I will be pharmaceutically acceptable salts. Other salts may, however, be useful in the preparation of the compounds according to the invention or of their pharmaceutically acceptable salts. When the compound of the present invention is acidic, suitable "pharmaceutically acceptable salts" refers to salts prepared form pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine caffeine, choline, N,N$^1$-dibenzylethylenediamine, diethylamin, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like. Preferred pharmaceutically acceptable salts are sodium and potassium salts. However, to facilitate isolation of the salt during preparation, salts which are less soluble in the chosen solvent may be preferred whether pharmaceutically acceptable or not.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric and tartaric acids.

The preparation of the pharmaceutically acceptable salts described above and other typical pharmaceutically acceptable salts is more fully described by Berg et al., "Pharmaceutical Salts," *J. Pharm. Sci.*, 1977:66:1-19.

In vivo hydrolysable esters are those pharmaceutically acceptable esters that hydrolyze in the human body to produce the parent compound. Such esters can be identified by administering, eg. Intravenously to a test animal, the compound under test and subsequently examining the test animal's body fluids.

As used herein, the term "composition" is intended to encompass a product comprising the specified ingredients in the specific amounts, as well as any product which results, directly or indirectly, from combination of the specific ingredients in the specified amounts.

When a compound according to this invention is administered into a human subject, the daily dosage will normally be determined by the prescribing physician with the dosage generally varying according to the age, weight, sex and response of the individual patient, as well as the severity of the patient's symptoms.

The maxi-K channel blockers used can be administered in a therapeutically effective amount intravaneously, subcutaneously, topically, transdermally, parenterally or any other method known to those skilled in the art.

Ophthalmic pharmaceutical compositions are preferably adapted for topical administration to the eye in the form of solutions, suspensions, ointments, creams or as a solid insert Ophthalmic formulations of this compound may contain from 0.01 ppm to 1% and especially 0.1 ppm to 1% of medicament. Higher dosages as, for example, about 10% or lower dosages can be employed provided the dose is effective in reducing intraocular pressure, treating glaucoma, increasing blood flow velocity or oxygen tension. For a single dose, from between 0.1 ng to 5000 ug, preferably 1 ng to 500 ug, and especially 10 ng to 100 ug of the compound can be applied to the human eye.

The pharmaceutical preparation which contains the compound may be conveniently admixed with a non-toxic pharmaceutical organic carrier, or with a non-toxic pharmaceutical inorganic carrier. Typical of pharmaceutically acceptable carriers are, for example, water, mixtures of water and water-miscible solvents such as lower alkanols or aralkanols, vegetable oils, polyalkylene glycols, petroleum based jelly, ethyl cellulose, ethyl oleate, carboxymethyl-cellulose, polyvinylpyrrolidone, isopropyl myristate and other conventionally employed acceptable carriers. The pharmaceutical preparation may also contain non-toxic auxiliary substances such as emulsifying, preserving, wetting agents, bodying agents and the like, as for example, polyethylene glycols 200, 300, 400 and 600, carbowaxes 1,000, 1,500, 4,000, 6,000 and 10,000, antibacterial components such as quaternary ammonium compounds, phenylmercuric salts known to have cold sterilizing properties and which are non-injurious in use, thimerosal, methyl and propyl paraben, benzyl alcohol, phenyl ethanol, buffering ingredients such as sodium borate, sodium acetates, gluconate buffers, and other conventional ingredients such as sorbitan monolaurate, triethanolamine, oleate, polyoxyethylene sorbitan monopalmitylate, dioctyl sodium sulfosuccinate, monothioglycerol, thiosorbitol, ethylenediamine tetracetic acid, and the like. Additionally, suitable ophthalmic vehicles can be used as carrier media for the present purpose including conventional phosphate buffer vehicle systems, isotonic boric acid vehicles, isotonic sodium chloride vehicles, isotonic sodium borate vehicles and the like. The pharmaceutical preparation may also be in the form of a microparticle formulation. The pharmaceutical preparation may also be in the form of a solid insert. For example, one may use a solid water soluble polymer as the carrier for the medicament. The polymer used to form the insert may be any water soluble non-toxic polymer, for example, cellulose derivatives such as methylcellulose, sodium carboxymethyl cellulose, (hydroxyloweralkyl cellulose), hydroxyethyl cellulose, hydroxypropyl cellulose, hydroxypropylmethyl cellulose; acrylates such as polyacrylic acid salts, ethylacrylates, polyactylamides; natural products such as gelatin, alginates, pectins, tragacanth, karaya, chondrus, agar, acacia; the starch derivatives such as starch acetate, hydroxymethyl starch ethers, hydroxypropyl starch, as well as other synthetic derivatives such as polyvinyl alcohol, polyvinyl pyrrolidone, polyvinyl methyl ether, polyethylene oxide, neutralized carbopol and xanthan gum, gellan gum, and mixtures of said polymer.

Suitable subjects for the administration of the formulation of the present invention include primates, man and other animals, particularly man and domesticated animals such as cats and dogs.

The pharmaceutical preparation may contain non-toxic auxiliary substances such as antibacterial components which are non-injurious in use, for example, thimerosal, benzalkonium chloride, methyl and propyl paraben, benzyldodecinium bromide, benzyl alcohol, or phenylethanol; buffering ingredients such as sodium chloride, sodium borate, sodium acetate, sodium citrate, or gluconate buffers; and other conventional ingredients such as sorbitan monolaurate, triethanolamine, polyoxyethylene sorbitan monopalmitylate, ethylenediamine tetraacetic acid, and the like.

The ophthalmic solution or suspension may be administered as often as necessary to maintain an acceptable IOP level in the eye. It is contemplated that administration to the mamalian eye will be about once or twice daily.

For topical ocular administration the novel formulations of this invention may take the form of solutions, gels, ointments, suspensions or solid inserts, formulated so that a unit dosage comprises a therapeutically effective amount of the active component or some multiple thereof in the case of a combination therapy.

The following examples given by way of illustration is demonstrative of the present invention.

Definitions of the terms used in the examples are as follows:
SM—Starting material,
DMSO—dimethyl sulfoxide,
TLC—thin layer chromatography,
SGC—silica gel chromatography,
PhMgBr—phenylmagnesiumbromide
h=hr=hour,
THF—tetrahydrofuran,
DMF—dimethylformamide,
min—minute,
LC/MS—liquid chromatography/mass spectrometry,
HPLC—high performance liquid chromatography,
PyBOP—Benzotriazol-1-yloxytris-dimethyl amino)phosphonium hexafluorophosphate,
equiv=eq=equivalent,
NBS—N-Bromosuccinamide and
AIBN—2,2'-azobisisobutyronitrile.

The compounds of this invention can be made, with modification where appropriate, in accordance with Schemes 1 through 3.

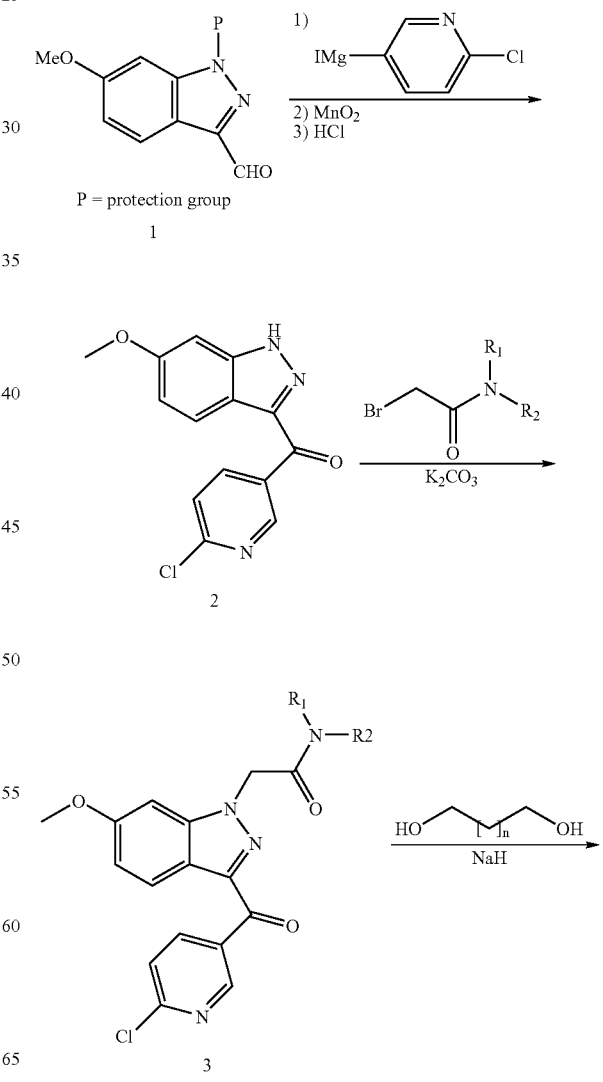

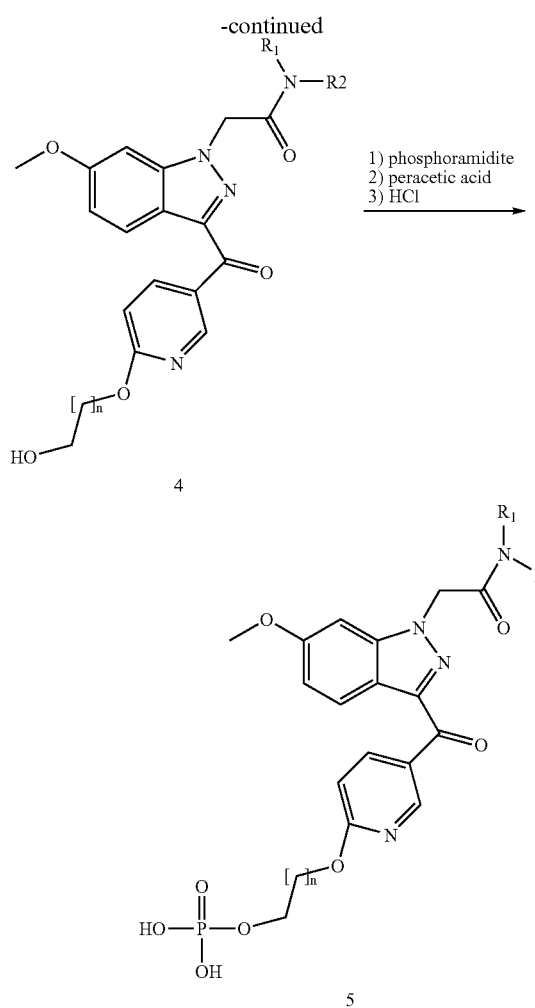
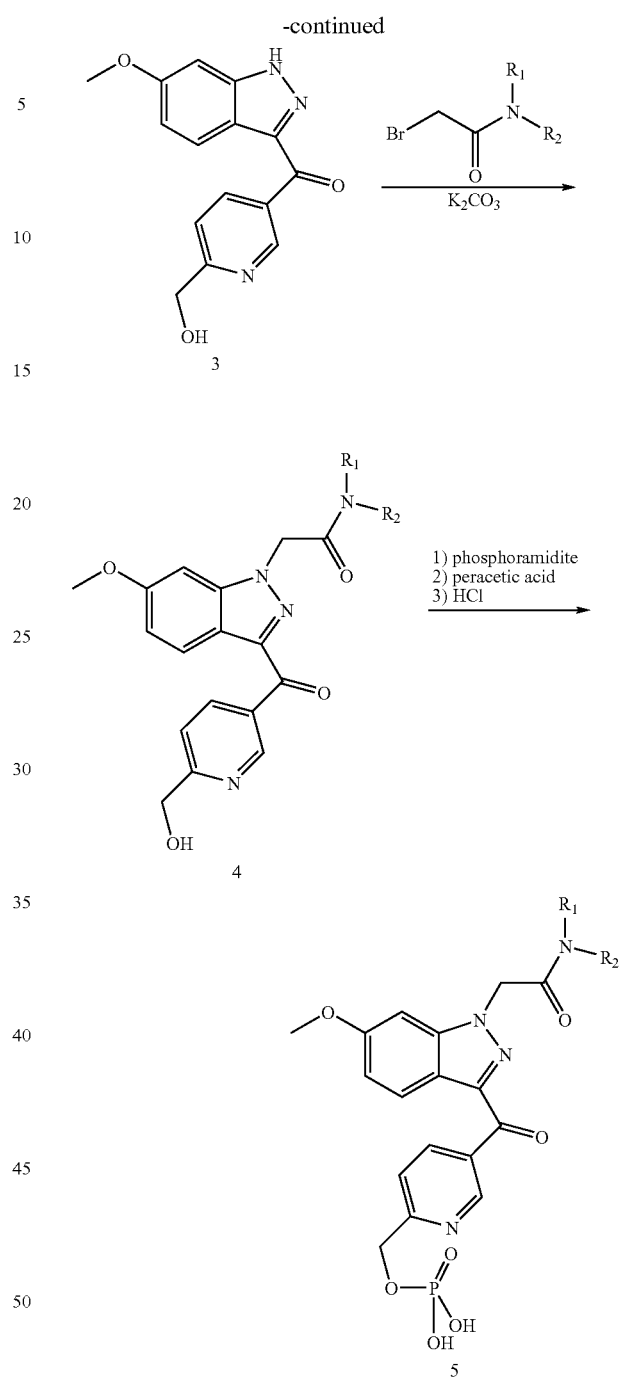
SCHEME 2
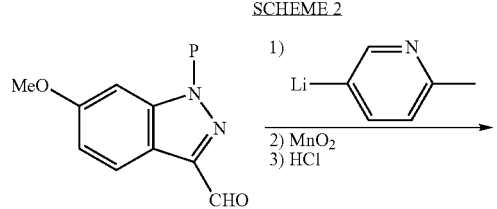
P = protection group
1
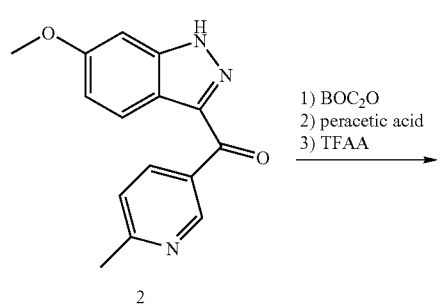
2
SCHEME 3
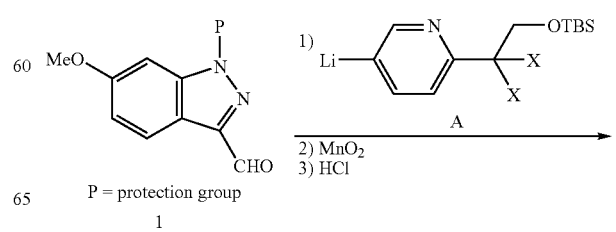

-continued

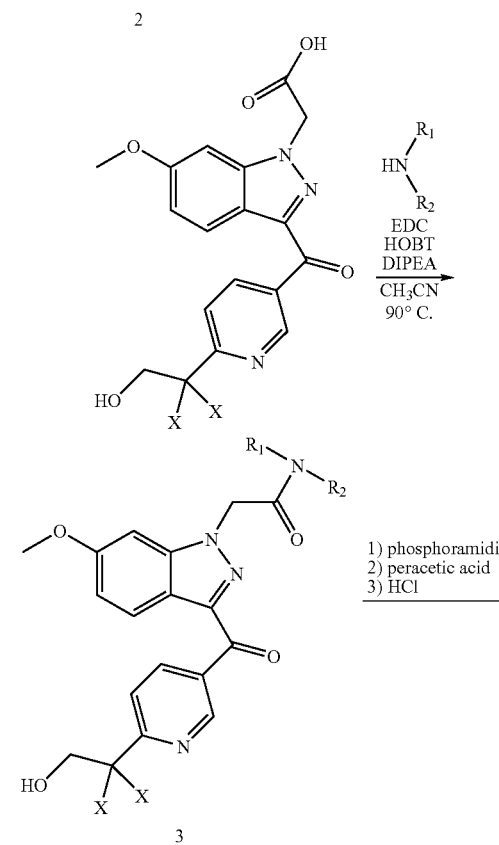

Intermediate 1

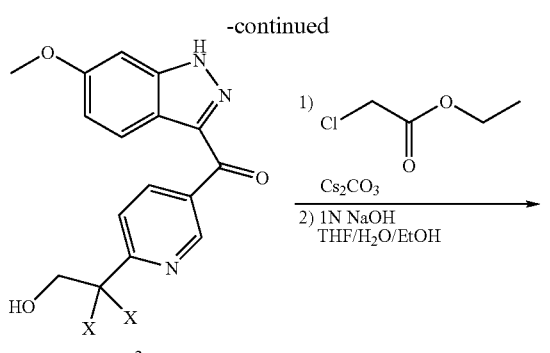

Step A:

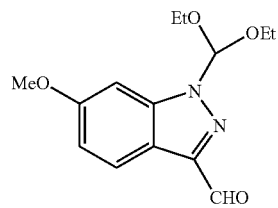

To a solution of dibromide (23.2 g, by-product of Example 1, step-3) in acetic acid was added sodium acetate (22.5 g). The mixture was placed in oil bath and refluxed for a couple of hours until reaction completed. The mixture was cooled to room temperature and then poured into ice/water to give desired compound as an off-white solid. The solid was isolated by filtration and dried over nitrogen atmosphere.

$^1$H NMR (CDCl$_3$): δ 10.23 (1H, s); 8.19 (1H, d); 7.02 (1H, dd); 6.96 (1H, d); 3.90 (3H, s).

Step B:

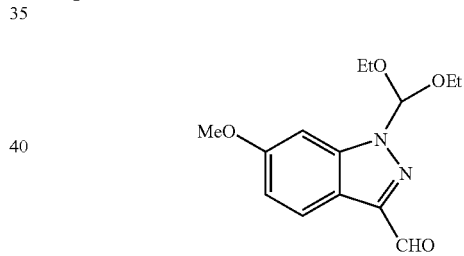

To the intermediate from Step A was added triethyl orthoformate (40 ml) and heated to 130° C. for a couple of hours. The resulting mixture was concentrated to dry to give title compound as a brown solid (11.9 g).

$^1$H NMR (DMSO): δ 10.08 (1H, s); 7.98 (1H, d); 7.25 (1H, d); 7.02 (1H, dd); 6.81 (1H, s); 3.82 (3H, s); 3.52 (4H, q); 1.11 (6H, t).

Intermediate 2

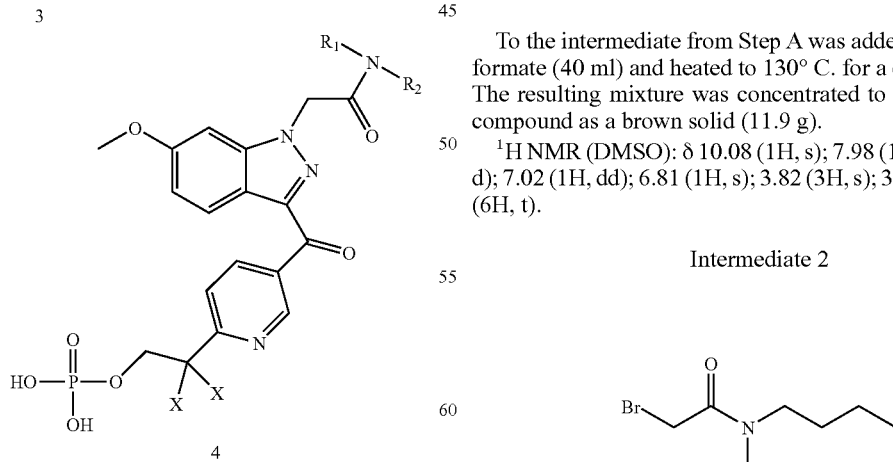

X = H, F

A solution of 1.99 g (10 mmol) of bromoacetate bromide in 20 mL of CH$_2$Cl$_2$ was cooled down to –78° C. and TEA (1.21 g, 12 mmol) was added dropwise. The reaction mixture stirred for 20 min before dibutyl amine (1.54 g, 12 mmol) was added dropwise. After reaction completed and the mixture was washed with 1N HCl, H$_2$O, brine, dried over MgSO$_4$, and concentrated in vacuo to yield a brown oil. The material was used without any further purification.

$^1$H NMR (CDCl$_3$) δ: 0.95 (6H, m), 1.35 (4H, m), 1.55 (4H, m), 3.30 (4H, m), 3.85 (2H, s).

Intermediate 3

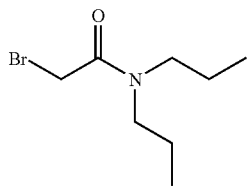

This intermediate was prepared as described in Intermediate 2, but dipropyl amine was used in place of dibutyl amine.

$^1$H NMR (CDCl$_3$) δ: 0.95 (6H, m), 1.60 (4H, m), 3.25 (4H, m), 3.82 (2H, s).

Intermediate 4

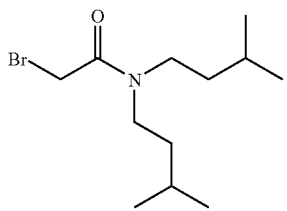

This intermediate was synthesized as described in Intermediate 2, but diisoamyl amine was used in place of dibutyl amine.

$^1$H NMR (CDCl$_3$) δ: 0.95 (12H, m), 1.40 (2H, m), 1.60 (4H, m), 3.30 (4H, m), 3.82 (2H, s).

Intermediate 5

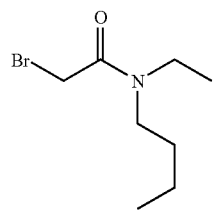

This intermediate was synthesized as described in Intermediate 2, but N,N-ethylbutyl amine was used in place of dibutyl amine.

$^1$H NMR (CDCl$_3$) δ: 0.95-0.99 (3H, m), 1.15-1.26 (3H, m), 1.35 (2H, m), 3.59 (2H, m), 3.30-3.40 (4H, m), 3.86 (2H, s).

Intermediate 6

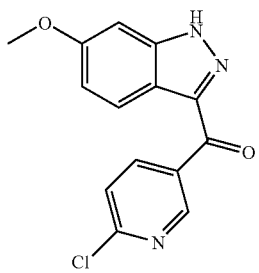

To a solution of 5-iodo-2-chloropyridine (2.56 g, 10.78 mmol) in THF (10 mL) was added iPrMgBr dropwise at –78° C. The reaction stirred for 1 h before Intermediate 1 (1.71 g, 6.10 mmol) was added as a solution in THF (5 mL). After 2 h and the reaction was quenched with 1N NaOH and extracted with EtOAc. The combined organic layers were washed with brine, dried over MgSO$_4$, and concentrated in vacuo. To a solution of the crude product in toluene (50 mL) was added MnO$_2$ (2.173 g, 25.0 mmol) and the reaction mixture was heated to 130° C. After 1 h the reaction was complete, filtered through a celite pad, and concentrated in vacuo. The crude product was dissolved in THF (10 mL) and 4 mL of 1N HCl was added dropwise. The reaction stirred at RT until TLC analysis indicated completion. The reaction mixture was cooled to 0° C. and the solid precipitate was collected (1.131 g, 64%). $^1$H NMR (CD$_3$OD) δ: 3.900 (3H, s), 7.013 (1H, d), 7.062 (1H, s), 7.627 (1H, d), 8.672 (1H, d), 9.306 (1H, s).

Intermediate 7

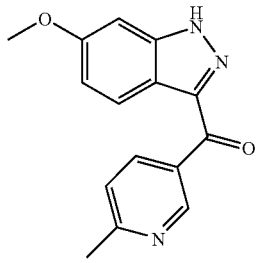

To a solution of 5-bromo-2-methylpyridine (736 mg, 4.31 mmol) in THF (15 mL) was added nBuLi dropwise (2.156 mL, 5.39 mmol, 2.5 M in hexanes) at –78° C. The reaction stirred for 1 h before Intermediate 1 (1.00 g, 3.59 mmol) was added as a solution in THF (5 mL). The starting material was consumed after 2 h and the reaction was quenched with 1N NaOH and extracted with EtOAc. The combined organic layers were washed with brine, dried over MgSO$_4$, and concentrated in vacuo. A solution of the crude product in toluene (20 mL) was added MnO$_2$ (0.414 g, 4.77 mmol) and the reaction mixture was heated to 130° C. After 1 h the reaction was complete, filtered through a celite pad, and concentrated in vacuo. The crude product was dissolved in THF and 4 mL of 1N HCl was added dropwise. After 1 h reaction mixture was cooled to 0° C. and the solid precipitate was collected (380 mg, 40.0%). $^1$H NMR (DMSO) δ: 2.553 (3H, s), 3.832

(3H, s), 7.000 (1H, d), 7.089 (1H, s), 7.451 (1H, d), 8.100 (1H, d), 8.430 (1H, d), 9.220 (1H, s).

Intermediate 8

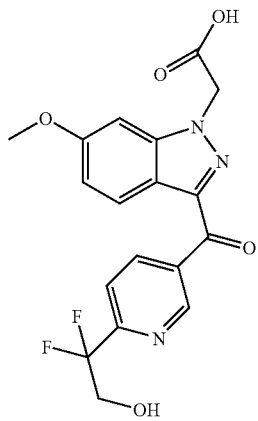

Step A:

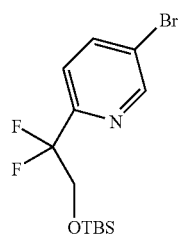

To a solution of 2-pyridineacetic acid, 5-bromo-α,α-difluoro-, ethyl ester (13.4 g; prepared according to "Ero, H.; Haneko, Y.; Sakamoto, T. *Chem Pharm. Bull.* 2000,48, 982.") in ethanol was added sodium borohydride (2.3 g) portionwise at 0° C. After stirring at 0° C. for 1 hour, the mixture was poured into water and extracted with ethyl acetate. The organic layer was washed with 1N NaOH$_{aq}$, brine, dried (MgSO$_4$), and concentrated under reduced pressure to afford crude alcohol. The crude alcohol in methylene chloride was added imidazole (4.1 g) and TBS-Cl (8.3 g) at 0° C. The mixture was stirred for 1 hour. The reaction was poured into 0.1 N HCl$_{aq}$ extracted with methylene chloride. The organic layer was washed with brine, dried (MgSO$_4$) and evaporated. The residue was purified by silica gel (100% methylene chloride) to give the desired compound as a colorless oil (13.5 g).

$^1$H NMR (CDCl$_3$): δ 8.75 (1H, d); 7.95 (1H, dd); 7.57 (1H, d); 4.20 (2H, t); 0.82 (9H, s); 0.02 (6H, s).

Step B:

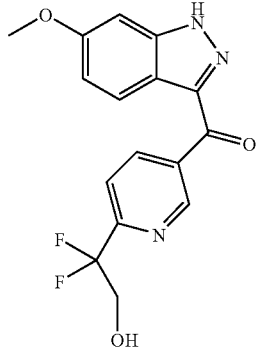

The desired compound was prepared by a procedure similar to the one described for Intermediate 7.

$^1$H NMR (DMSO): δ 9.35 (1H, d); 8.65 (1H, dd); 8.14 (1H, d); 7.88 (1H, d); 7.10 (1H, d); 7.03 (1H, dd); 4.05 (2H, t); 3.85 (3H, s).

LC-MS (M+H)=334.2.

Step C:

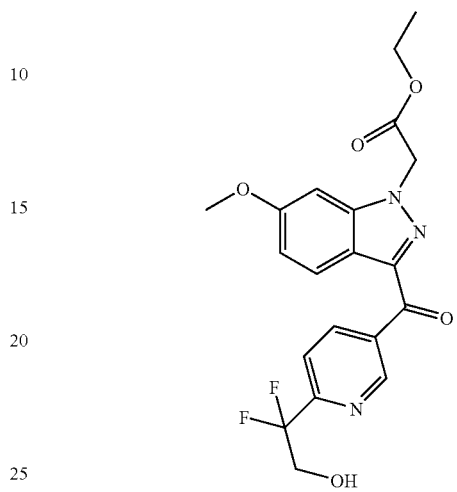

To a solution of the intermediate from Step B (200 mg, 0.602 mmol) and Cs$_2$CO$_3$ (586 mg, 1.806 mmol) in DMF (4 mL) was added ethyl bromoacetate (0.134 mL, 1.204 mmol). After 40 min the reaction was complete and quenched with H$_2$O. The reaction mixture was extracted with EtOAc and the combined organic layers were washed with H$_2$O, brine, dried over MgSO$_4$, and concentrated in vacuo. The material was used with no further purification.

$^1$H NMR (CDCl$_3$) δ: 1.286 (3H, m), 3.915 (3H, s), 4.296 (4H, m), 5.209 (2H, s), 6.738 (1H, s), 7.063 (1H, d), 7.871 (1H, d), 8.310 (1H, d), 8.708 (1H, d), 9.527 (1H, s).

Step D:

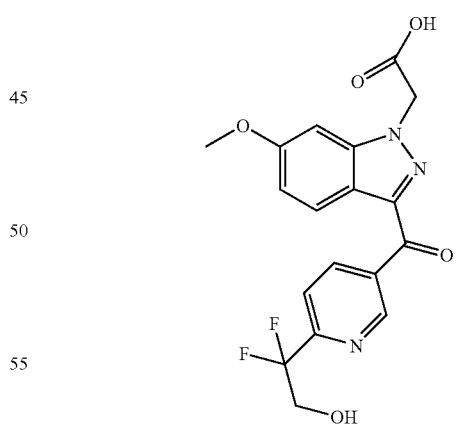

To a solution of the intermediate from Step C was added 12 mL of THF/EtOMH/H$_2$O (1:1:1) followed by the addition of 150 mg of NaOH. After 1 h the reaction was complete and the THF and EtOAc were removed in vacuo. The aqueous layer was extracted with ether, acidified to pH 2, diluted with EtOAc, washed with H$_2$O, dried over MgSO$_4$, and concentrated in vacuo. The crude product was used with no further purification.

$^1$H NMR (CD$_3$OD) δ: 3.909 (3H, s), 4.157 (2H, t), 5.374 (2H, s), 7.027 (1H, d), 7.103 (1H, s), 7.881 (1H, d), 8.201 (1H, d), 8.764 (1H, d), 9.462 (1H, s).

Intermediate 9

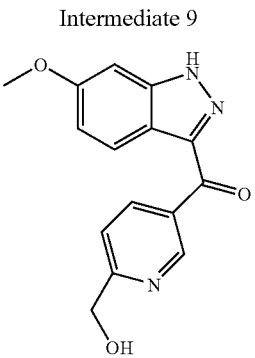

To a stirring solution of Intermediate 7 (275 mg, 1.02 mmol) in CH$_3$N was added TEA (0.169 mL, 1.22 mmol), DMAP (12 mg, 0.102 mmol), and tert-butoxycarbonyl anhydride (265 mg, 1.22 mmol). After 30 min the reaction was diluted with EtOAc and extracted with H$_2$O, brine, dried over MgSO$_4$, and condensed in vacuo. To the crude material was added peracetic acid (0.159 mL, 1.278 mmol) at 0° C. TLC indicated the reaction was complete after 1.5 h and the reaction mixture was concentrated in vacuo. The crude material was purified via silica gel chromatography. The N-oxide was dissolved in CH$_2$Cl$_2$ and TFAA was added dropwise at 0° C. The reaction warmed up to RT and stirred overnight. To the completed reaction was diluted with H$_2$O and EtOAc and the pH was adjusted to 13-14 with 1N NaOH. The aqueous layer was washed with EtOAc and the combined organic layers were washed with H$_2$O, brine, dried over MgSO$_4$, and condensed in vacuo to yield the desired product (52 mg, 18%).

$^1$H NMR (CDCl$_3$) δ: 3.90 (3H, s), 4.95 (2H, s), 6.85 (1H, s), 7.05 (1H, d), 7.50 (1H, d), 8.30 (1H, d), 8.68 (1H, d), 9.64 (1H, s).

Intermediate 10

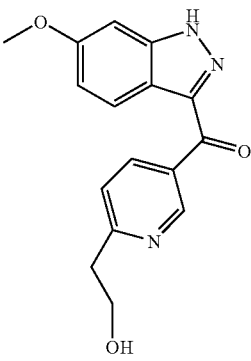

Step A:

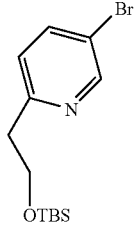

To a solution of 2,5-dibromopyridine (2.4 g) in toluene was added tributylallyltin (3.4 ml) and dichlorobis(triphenylphosphine) palladium (0.7 g) under nitrogen atmosphere. The mixture was refluxed for a couple of hours and concentrated under reduced pressure. The residue was re-dissolved in "wet ether" and added DBU (3 ml) slowly to give a cloudy solution. The mixture was filtered over a pad of silica gel and concentrated. The residue was dissolved in methylene chloride/methanol=1/1 solution and cooled to −78° C. To this solution was bubbled though ozone until the reaction mixture became a blue color. The reaction was warmed to 0° C. and added sodium borohydride (0.5 g) portion-wise. After stirring at 0° C. for 1 hour, the mixture was poured into water and extracted with ethyl acetate. The organic layer was washed with 1N NaOH$_{aq}$, brine, dried (MgSO$_4$), and concentrated under reduced pressure to afford crude alcohol. The alcohol was purified by silica gel (methylene chloride/ethyl acetate=1/1) to give desired alcohol. To a solution of alcohol in methylene chloride was added imidazole (0.4 g) and TBS-Cl (0.8 g) at 0° C. The mixture was stirred for 1 hour. The reaction was poured into 0.1 N HCl$_{aq}$ extracted with methylene chloride. The organic layer was washed with brine, dried (MgSO$_4$) and evaporated. The residue was purified by silica gel (100% methylene chloride) to give desired compound (1.05 g).

$^1$H NMR (CDCl$_3$): δ 8.61 (1H, d); 7.73 (1H, dd); 7.14 (1H, d); 3.97 (2H, t); 2.96 (2H, t); 0.86 (9H, s); −0.02 (6H, s).

Step B:

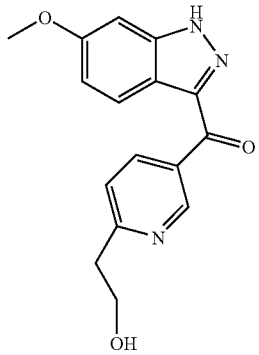

The Intermediate 10 was prepared by the procedure similar to the one described for Intermediate 7. The desired intermediate 10 was precipitate out in pH>10.

$^1$H NMR (DMSO): δ 9.23 (1H, d); 8.43 (1H, dd); 8.11 (1H, d); 7.46 (1H, d); 7.04 (1H, dd); 6.99 (1H, d); 4.85 (2H, t); 3.83 (3H, s); 2.97 (2H, t).

LC-MS (M+H)=298.4

EXAMPLE 1

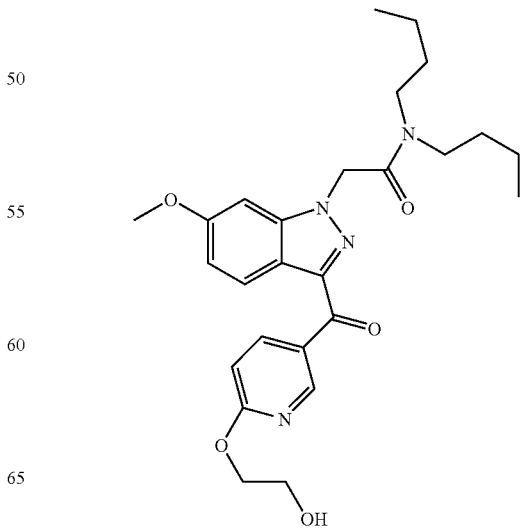

23

Step A:

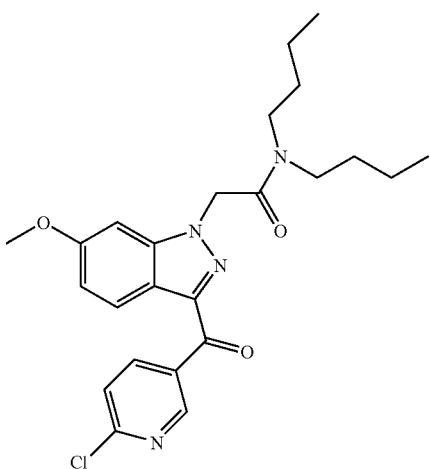

To a solution of Intermediate 6 (600 mg g, 2.08 mmol) and Cs₂CO₃ (2.028 g, 6.24 mmol) in DMF (14 mL) was added Intermediate 2 (809 mg, 3.24 mmol). After 35 min the reaction was complete and poured into ice water. The solid precipitate was collected to yield 950 mg of the desired product (quantitative).

$^1$H NMR (CDCl₃) δ: 0.919 (3H, t), 0.975 (3H, t), 1.327 (4H, m), 1.596 (4H, m), 3.408 (4H, m), 3.926 (3H, s), 5.275 (2H, s), 6.864 (1H, s), 7.053 (1H, d), 7.491 (1H, d), 8.321 (1H, d), 8.563 (1H, d), 9.425 (1H, d).

Step B:

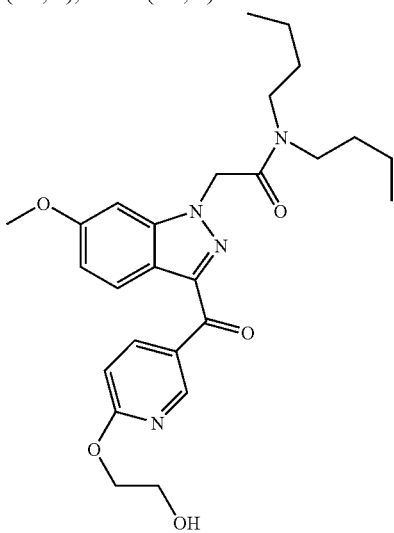

800 mg (20.0 mmol) of NaH (60% dispersion in mineral oil) was washed 3× with hexane and dried under nitrogen. Ethylene glycol (14 mL) was added to the dry NaH and the reaction stirred for 20 min at 50° C. To the reaction mixture was added the intermediate from the previous step (916 mg, 2.0 mmol) as a solution in THF (12 mL). The reaction was stirred over night at 50° C. The reaction mixture was poured into ice water and the solid precipitate was collected. The crude product was purified via silica gel chromatography to yield the desired product (688 mg, 71.1%).

H NMR (CDCl₃) δ: 0.903 (3H, m), 0.987 (3H, m), 1.372 (4H, m), 1.584 (4H, m), 3.405 (4H, m), 3.922 (3H, s), 4.028 (2H, m), 4.640 (2H, m), 5.288 (2H, s), 6.858 (1H, s), 6.953 (1H, d), 7.050 (1H, d), 8.302 (1H, d), 8.579 (1H, d), 9.360 (1H, s).

24

EXAMPLE 2

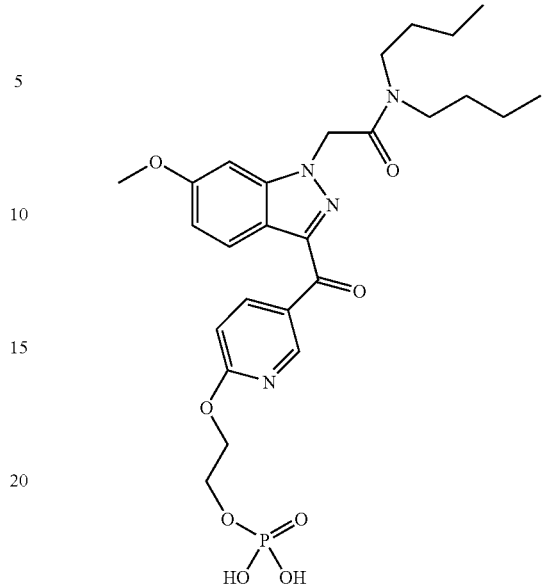

To a solution of the intermediate from Example 1, Step B (438 mg, 0.908 mmol) in CHCl₃ (10 mL) was added tetrazole (3.02 mL, 1.362 mmol, 0.45 M/CH₃CN) and di-tert-butyl diethylphosphoramidite (0.302 mL, 1.09 mmol) at RT. After 0.5 h the reaction was complete and peracetic acid (0.227 mL, 1.816 mmol) was added at 0° C. for 0.5 h. The reaction mixture was quenched with saturated sodium bisulfite, diluted with EtOAc, washed with saturated sodium bicarbonate, H₂O, and saturated NaCl, dried over MgSO₄, and evaporated to dryness in vacuo. The crude residue was chromatographed on SiO₂ to yield 398 mg of pure product. To the phosphate ester dissolved in EtOAc was bubbled 99% HCl (g) at 0° C. until saturation. The solid precipitate was collected to yield 170 mg of the final product. Further recrystallization of the mother liquor from MeOH/tOAc/hexane yielded 140 mg more of the final product. 310 mg collected (82% yield).

$^1$H NMR (CD₃OD) δ: 0.922 (3H, t), 1.004 (3H, t), 1.312 (2H, m), 1.408 (2H, m) 1.554 (2H, m), 1.651 (2H, m), 3.386 (2H, t), 3.516 (2H, t), 3.904 (3H, s), 4.335 (2H, m), 4.629 (2H, m), 5.487 (2H, s), 6.933 (1H, d), 6.998 (1H, d), 7.040 (1H, s), 8.196 (1H, d), 8.566 (1H, d), 9.215 (1H, s).

EXAMPLE 3

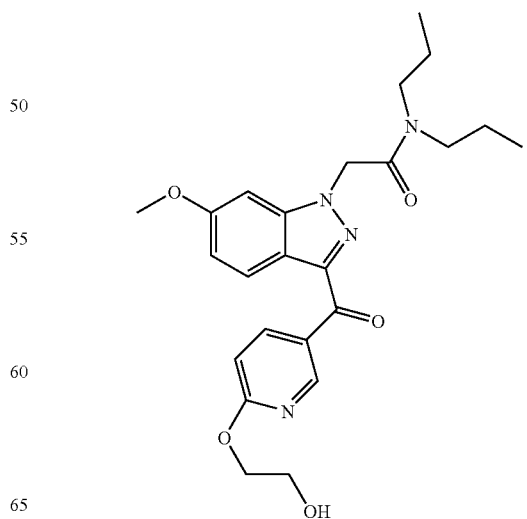

Step A:

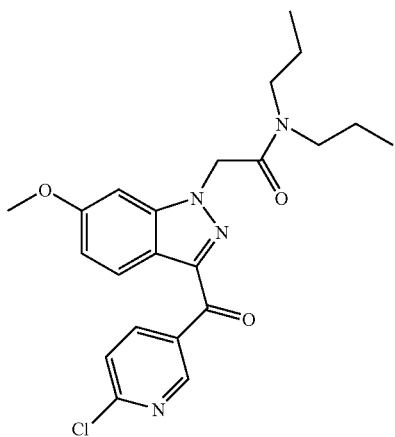

This compound was prepared as described in Step A of Example 1 but Intermediate 3 was used in place of Intermediate 2.

$^1$H NMR (CDCl$_3$) δ: 0.832 (3H, t), 0.992 (3H, t), 1.667 (4H, m), 3.384 (4H, m), 3.866 (3H, s), 5.218 (2H, s), 6.777 (1H, s), 6.937 (1H, d), 7.365 (1H, m), 8.178 (1H, d), 8.495 (1H, d), 9.377 (1H, s).

Step B:

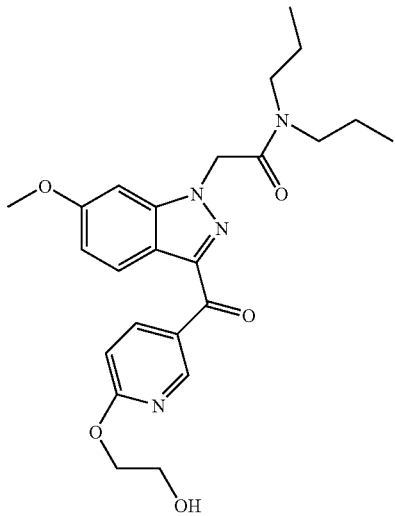

This compound was prepared as described in Step B of Example 1. Purified via SiO$_2$ preparatory plate (1:2 hexane/EtOAc).

$^1$H NMR (CDCl$_3$) δ: 0.843 (3H, t), 0.975 (3H, t), 1.619 (4H, m), 3.400 (4H, m), 3.917 (3H, s), 4.010 (2H, m), 4.109 (2H, m), 5.291 (2H, s), 6.858 (1H, s), 6.927 (1H, d), 7.046 (1H, d), 8.318 (1H, d), 8.569 (1H, d), 9.330 (1H, s).

EXAMPLE 4

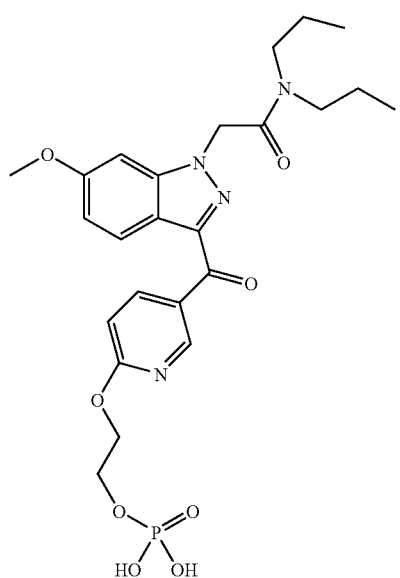

This compound was prepared as described in Example 2. Purified via reverse phase chromatography (10-90% acetonitrile in H$_2$O).

$^1$H NMR (CD$_3$OD) δ: 0.876 (3H, m), 1.003 (3H, m), 1.599 (2H, m), 1.705 (2H, m), 3.028 (2H, bs), 3.460 (2H, bs), 3.882 (3H, s), 4.286 (2H, bs), 4.585 (2H, bs), 5.441 (2H, s), 6.990 (3H, m), 8.143 (1H, d), 8.520 (1H, d), 9.146 (1H, s).

EXAMPLE 5

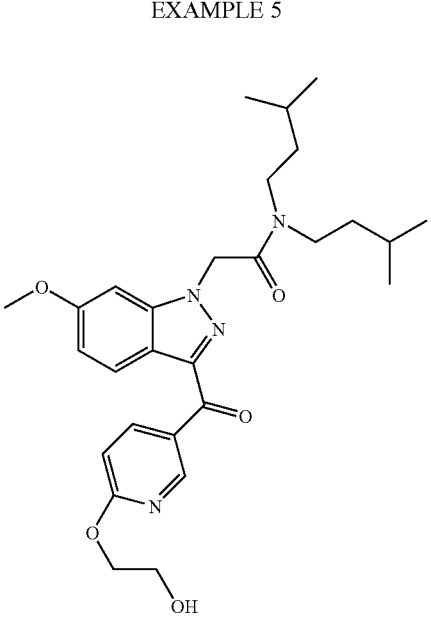

Step A:

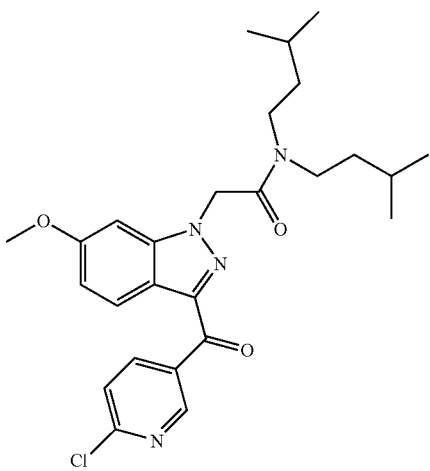

This compound was prepared as described in Step A of Example 1 but Intermediate 4 was used in place of Intermediate 2.

$^1$H NMR (CDCl$_3$) δ: 0.857 (6H, d), 0.943 (6H, d), 1.380-1.604 (6H, m), 3.338 (4H, m), 3.834 (3H, s), 5.196 (2H, s), 6.748 (1H, s), 6.974 (1H, d), 7.400 (1H, d), 8.208 (1H, d), 8.503 (1H, d), 9.336 (1H, s).

Step B:

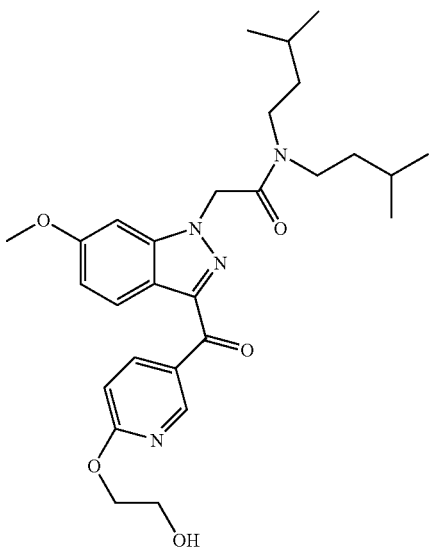

This compound was prepared as described in Step B of Example 1. Purified via SiO$_2$ preparatory plate (1:1 hexane/EtOAc).

$^1$H NMR (CDCl$_3$) δ: 0.909 (6H, d), 0.975 (6H, d), 1.503-1.624 (6H, m), 3.441 (4H, m), 3.925 (3H, s), 4.032 (2H, m), 4.610 (2H, m), 5.282 (2H, s), 6.863 (1H, s), 6.954 (1H, d), 7.054 (1H, s), 8.324 (1H, d), 8.585 (1H, d), 9.354 (1H, s).

EXAMPLE 6

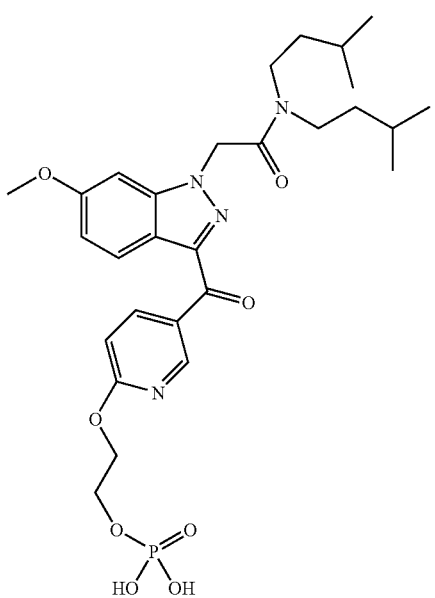

This compound was prepared as described in Example 2. Purified via reverse phase chromatography (10-90% acetonitrile in H$_2$O).

$^1$H NMR (CD$_3$OD) δ: 0.922 (6H, d), 0.971 (6H, d), 1.462 (2H, m), 1.563 (4H, m), 3.414 (2H, m), 3.503 (2H, m), 3.907 (3H, s), 4.340 (2H, bs), 4.629 (2H, bs), 5.474 (2H, s), 6.952 (1H, d), 7.000 (1H, d), 7.058 (1H, s), 8.197 (1H, d), 8.546 (1H, d), 9.211 (1H, s).

EXAMPLE 7

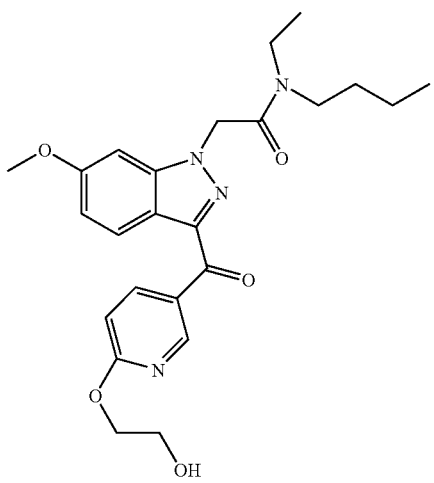

Step A:

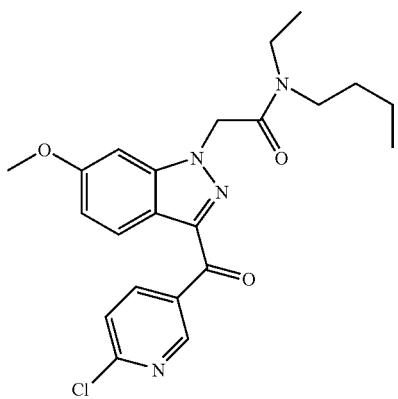

This compound was prepared as described in Step A of Example 1 but Intermediate 4 was used in place of Intermediate 2.

Step B:

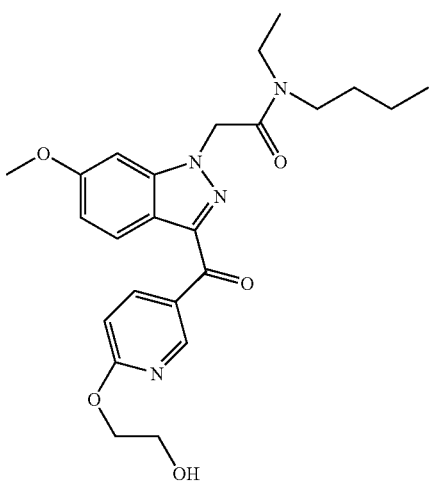

This compound was prepared as described in Step B of Example 1. Purified via SiO$_2$ preparatory plate (1:1 hexane/EtOAc).

$^1$H NMR (CDCl$_3$) δ: 0.919 (m, 3H), 1.148-1.370 (5H, m), 1.572 (2H, m), 3.445 (4H, m), 3.914 (3H, s), 4.008 (2H, m), 4.603 (2H, m), 5.275 (2H, s), 6.848 (1H, d), 6.916 (1H, d), 7.019 (1H, d), 8.290 (1H, d), 8.542 (1H, m), 9.316 (1H, s).

EXAMPLE 8

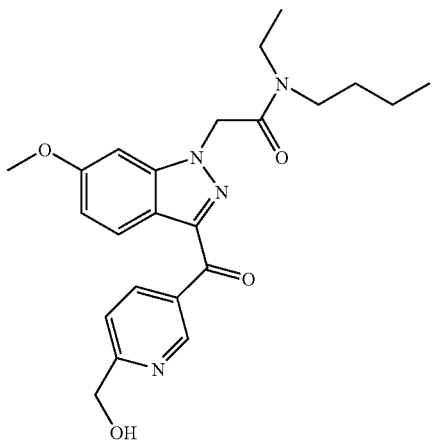

Using Intermediate 9, this compound was prepared as described in Step A of Example 1 but Intermediate 5 was used in place of Intermediate 2. Purified via SiO$_2$ preparatory plate chromatography.

$^1$H NMR (CDCl$_3$) δ: 0.924 (3H, m), 1.158-1.440 (7H, m), 3.442 (4H, m), 3.932 (3H, s), 4.956 (2H, s), 5.310 (2H, s), 6.871 (1H, s), 7.081 (1H, d), 7.559 (1H, d), 8.314 (1H, d), 8.712 (1H, d), 9.673 (1H, s).

EXAMPLE 9

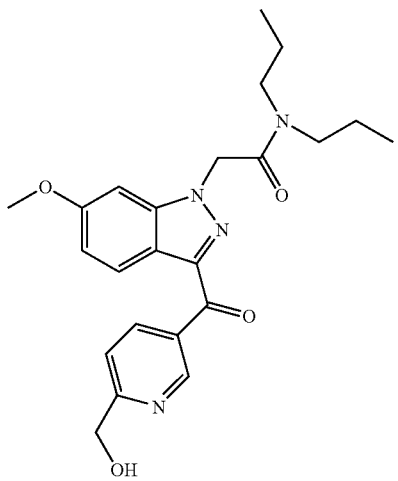

Using Intermediate 9, this compound was prepared as described in Step A of Example 1 but Intermediate 3 was used in place of Intermediate 2. Purified via SiO$_2$ preparatory plate chromatography.

$^1$H NMR (CDCl$_3$) δ: 0.895 (3H, t), 0.993 (3H, t), 1.653 (4H, m), 3.335 (4H, m), 3.926 (3H, s), 4.942 (s, 2H), 5.310 (2H, s), 6.859 (1H, s), 7.077 (1H, d), 7.519 (1H, d), 8.312 (1H, d), 8.694 (1H, d), 9.651 (1H, s).

EXAMPLE 10

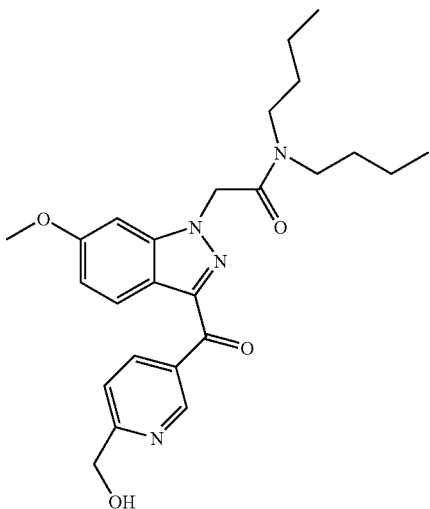

Using Intermediate 9, this compound was prepared as described in Step A of Example 1. Purified via $SiO_2$ preparatory plate chromatography.

$^1$H NMR (CDCl$_3$) δ: 0.916 (3H, t), 0.965 (3H, t), 1.379 (4H, m), 1.589 (4H, m), 3.414 (4H, m), 3.925 (3H, s), 4.896 (2H, m), 5.285 (2H, s), 6.865 (1H, s), 7.045 (1H, d), 7.443 (1H, d), 8.311 (1H, d), 8.615 (1H, d), 9.578 (1H, s).

EXAMPLE 11

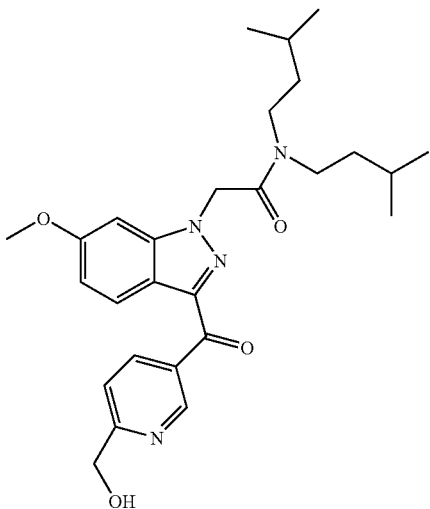

Using Intermediate 9, this compound was prepared as described in Step A of Example 1 but Intermediate 4 was used in place of Intermediate 2. Purified via $SiO_2$ preparatory plate chromatography.

$^1$H NMR (CDCl$_3$) δ: 0.910 (6H, d), 0.992 (6H, d), 1.450-1.700 (6H, m), 3.411 (4H, m), 3.933 (3H, s), 4.973 (2H, s), 5.297 (2H, s), 6.847 (1H, s), 7.082 (1H, d), 7.568 (1H, bs), 8.332 (1H, d), 8.744 (1H, bs), 9.701 (1H, s).

EXAMPLE 12

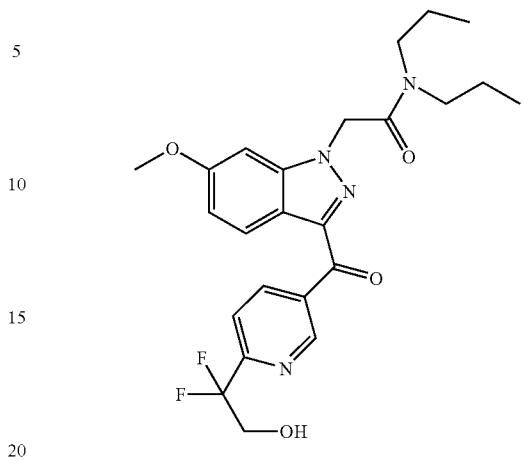

To Intermediate 8 (21 mg, 0.053 mmol), HOBt (14.3 mg, 0.106 mmol), and EDC (30.3 mg, 0.159 mmol) was added NMP (1 mL) and DIPEA (0.027 mL, 0.159 mmol). After 10 min dipropyl amine (0.014 mL, 0.106 mmol) was added to the reaction and the mixture stirred overnight at RT. Upon completion the reaction was diluted with water and extracted with EtOAc. The combined organic layers were washed with 1N HCl, water, brine, dried over MgSO$_4$, and concentrated in vacuo. The final product was purified via reverse phase liquid chromatography (25-100% acetonitrile in H$_2$O).

$^1$H NMR (CDCl$_3$) δ: 0.882 (3H, t), 1.01 (3H, t), 1.654 (4H, m), 3.368 (4H, m), 3.925 (3H, s), 4.311 (2H, t), 5.292 (2H, s), 6.858 (1H, s), 7.068 (1H, d), 7.866 (1H, d), 8.318 (1H, d), 8.724 (1H, d), 9.539 (1H, s).

EXAMPLE 13

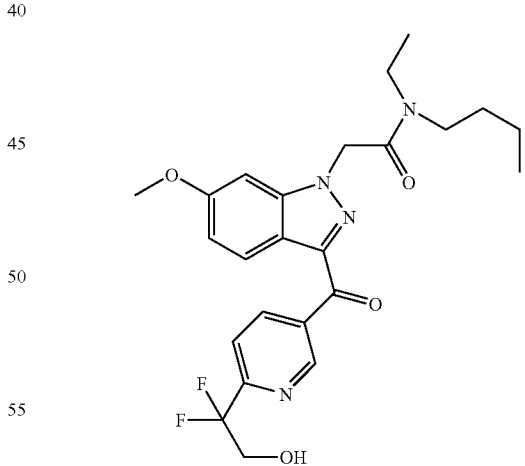

This compound was made as described in Example 12 but N—N-ethylbutyl amine was used in place of dipropyl amine. The product was purified via silica gel preparatory plate chromatography (EtOAc/hexane=1/1).

$^1$H NMR (CDCl$_3$) δ: 0.924 (3H, m), 1.152-1.593 (7H, m), 3.451 (4H, m), 3.928 (3H, s), 4.306 (2H, t), 5.277 (2H, s), 6.877 (1H, d), 7.081 (1H, d), 7.881 (1H, d), 8.316 (1H, d), 8.732 (1H, d), 9.539 (1H, s).

EXAMPLE 14

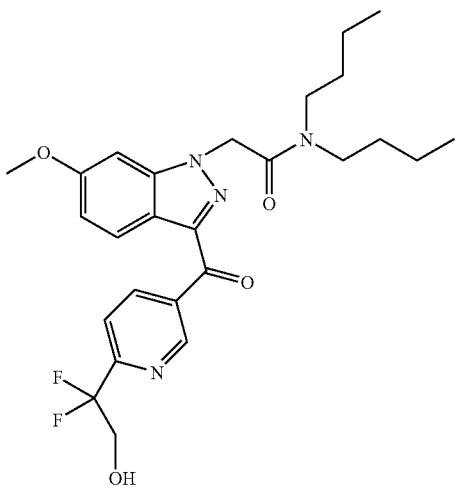

This compound was made as described in Example 12 but dibutyl amine was used in place of dipropyl amine. The product was purified via silica gel chromatography (EtOAc/hexane=1/1).

$^1$H NMR (CHCl$_3$): δ 9.55 (1H, d); 8.73 (1H, dd); 8.32 (1H, d); 7.88 (1H, d); 7.07 (1H, dd); 6.86 (1H, d); 5.29 (2H, s); 4.32 (2H, t); 3.93 (3H, s); 3.38 (4H, m); 1.60 (4H, m); 1.40-1.28 (4H, m); 0.97 (3H, t); 0.92 (3H, t).

LC-MS (M+H)=503.7.

EXAMPLE 15

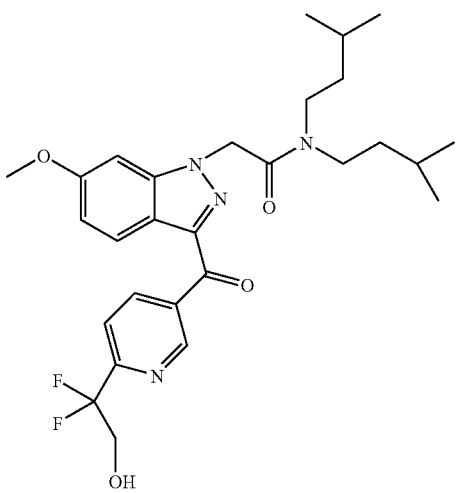

This compound was made as described in Example 12 but diisoamyl amine was used in place of dipropyl amine. The product was purified via silica gel chromatography (EtOAc/hexane=1/1).

$^1$H NMR (CHCl$_3$): δ 9.55 (1H, d); 8.73 (1H, dd); 8.33 (1H, d); 7.88 (1H, d); 7.07 (1H, dd); 6.87 (1H, d); 5.27 (2H, s); 4.32 (2H, t); 3.94 (3H, s); 3.40 (4H, m); 1.67-1.43 (6H, m); 0.97 (6H, d); 0.92 (6H, d).

LC-MS (M+H)=531.3

EXAMPLE 16

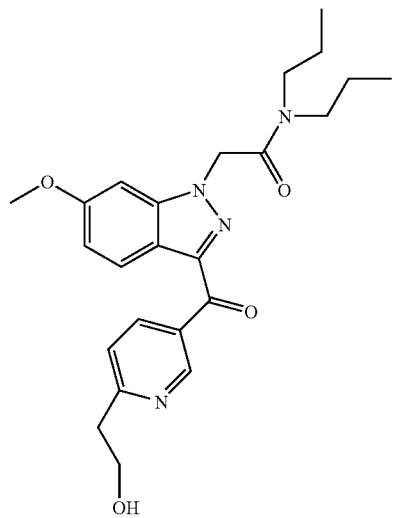

To a solution of Intermediate 10 (150 mg) and Cs$_2$CO$_3$ (500 mg) in DMF was added Intermediate 3 (150 mg). After reaction completed, the mixture was poured into ice/water to give precipitate. This compound was purified by silica gel (methylene chloride/ethyl acetate=1/1).

$^1$H NMR (CHCl$_3$): δ 9.53 (1H, d); 8.54 (1H, dd); 8.31 (1H, d); 7.36 (1H, d); 7.05 (1H, dd); 6.86 (1H, d); 5.30 (2H, s); 4.11 (2H, t); 3.92 (3H, s); 3.40 (2H, t); 3.35 (2H, t); 3.17 (2H, m); 1.61 (4H, m); 0.098 (3H, t); 0.89 (3H, t).

LC-MS (M+H)=439.2.

EXAMPLE 17

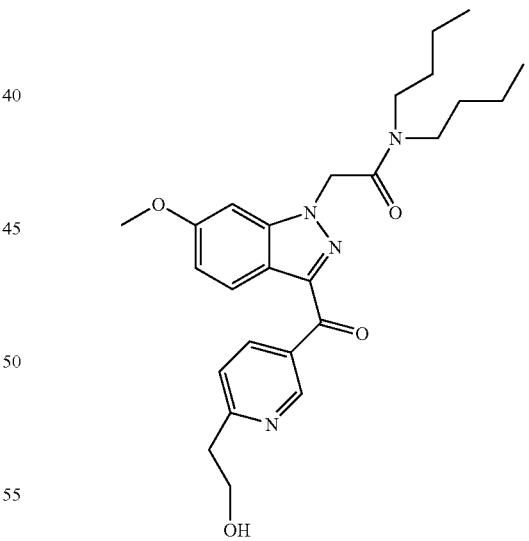

The desired compound was prepared by the procedure described in Example 16 using Intermediate 2 instead of Intermediate 3. This compound was purified by silica gel (methylene chloride/ethyl acetate=1/1).

$^1$H NMR (CHCl$_3$): δ 9.57 (1H, d); 8.57 (1H, dd); 8.32 (1H, d); 7.39 (1H, d); 7.06 (1H, dd); 6.86 (1H, d); 5.30 (2H, s); 4.11 (2H, t); 3.93 (3H, s); 3.42 (2H, t); 3.38 (2H, t); 3.20 (2H, m); 1.57 (4H, m); 1.40-1.28 (4H, m); 0.98 (3H, t); 0.92 (3H, t).

LC-MS (M+H)=467.4.

EXAMPLE 18

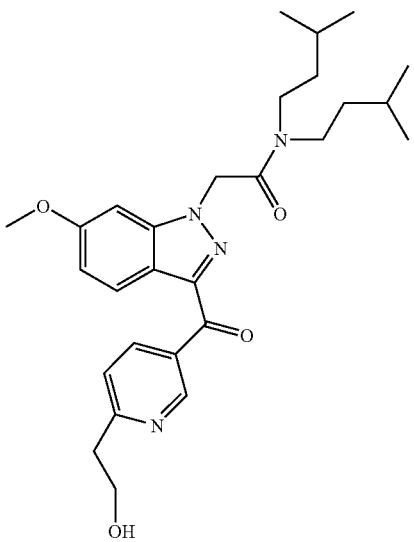

The desired compound was prepared by the procedure described in Example 16 using Intermediate 4 instead of Intermediate 3. This compound was purified by silica gel (hexanes/ethyl acetate=1/3).

$^1$H NMR (CHCl$_3$): δ 9.58 (1H, d); 8.58 (1H, dd); 8.32 (1H, d); 7.41 (1H, d); 7.06 (1H, dd); 6.86 (1H, d); 5.29 (2H, s); 4.11 (2H, t); 3.93 (3H, s); 3.40 (4H, m); 3.22 (2H, m); 1.74-1.40 (6H, m); 0.98 (6H, t); 0.92 (6H, t).

LC-MS (M+H)=495.4.

EXAMPLE 19

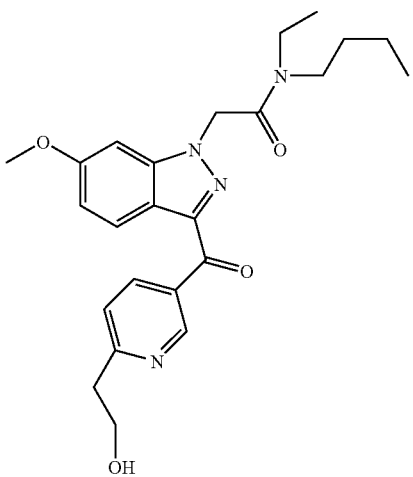

The desired compound was prepared by the procedure described in Example 16 using Intermediate 5 instead of Intermediate 3. This compound was purified by silica gel (methylene chloride/ethyl acetate=3/5).

$^1$H NMR (CHCl$_3$): δ 9.51 (1H, d); 8.51 (1H, dd); 8.32 (1H, d); 7.33 (1H, d); 7.05 (1H, dd); 6.86 (1H, d); 5.29 (2H, s); 4.11 (2H, t); 3.93 (3H, s); 3.53-3.36 (4H, m); 3.14 (2H, m); 1.56 (2H, m); 1.32 (2H, m); 1.22 (3/2H, t); 1.17 (3/2H, t); 0.96 (3/2H, t); 0.92 (3/2H, t). LC-MS (M+H)=439.4.

EXAMPLE 20

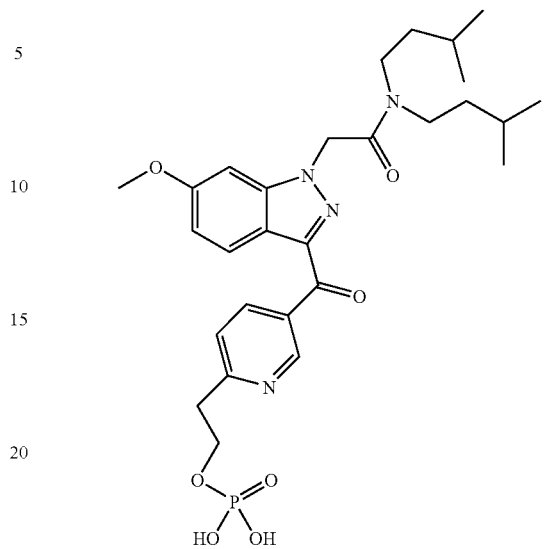

This compound was prepared as described in Example 2 from the compound synthesized in Example 18. The compound was recrystallized from isopropanol.

$^1$H NMR (CD$_3$OD) δ: 0.909 (6H, d), 0.998 (6H, d), 1.477 (2H, m), 1.591 (4H, m), 3.383 (2H, m), 3.487 (2H, m), 3.520 (2H, m), 3.915 (3H, s), 4.386 (2H, m), 5.516 (2H, s), 7.033 (2H, m), 7.761 (1H, d), 8.211 (1H, d), 8.824 (1H, d), 9.470 (1H, s).

EXAMPLE 21

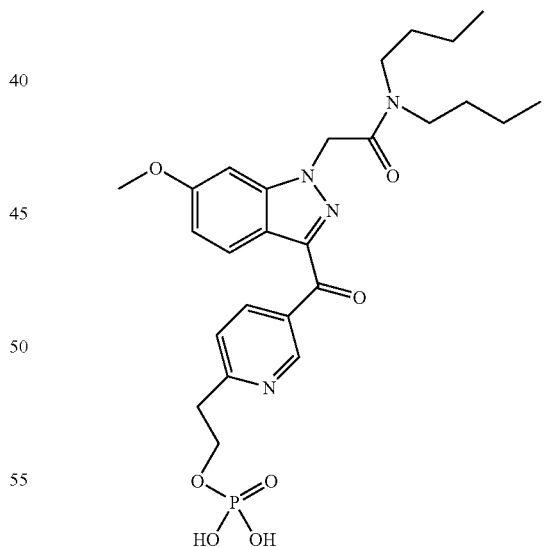

This compound was prepared as described in Example 2 from the compound synthesized in Example 17. The compound was recrystallized from isopropanol.

$^1$H NMR (CD$_3$OD) δ: 0.910 (3H, t), 1.000 (3H, t), 1.345 (2H, m), 1.431 (2H, m), 1.584 (2H, m), 1.708 (2H, m), 3.403 (4H, m), 3.519 (2H, t), 3.914 (3H, s), 4.402 (2H, m), 5.544 (2H, s), 7.065 (2H, m), 7.971 (1H, d), 8.232 (1H, d), 9.079 (1H, d), 9.555 (1H, s).

Functional Assays

A. Maxi-K Channel

The activity of the compounds can also be quantified by the following assay.

The identification of inhibitors of the Maxi-K channel is based on the ability of expressed Maxi-K channels to set cellular resting potential after transfection of both alpha and beta1 subunits of the channel in HEK-293 cells and after being incubated with potassium channel blockers that selectively eliminate the endogenous potassium conductances of HEK-293 cells. In the absence of maxi-K channel inhibitors, the transfected HEK-293 cells display a hyperpolarized membrane potential, negative inside, close to $E_K$ (−80 mV) which is a consequence of the activity of the maxi-K channel. Blockade of the Maxi-K channel by incubation with maxi-K channel blockers will cause cell depolarization. Changes in membrane potential can be determined with voltage-sensitive fluorescence resonance energy transfer (FRET) dye pairs that use two components, a donor coumarin ($CC_2DMPE$) and an acceptor oxanol ($DiSBAC_2(3)$).

Oxanol is a lipophilic anion and distributes across the membrane according to membrane potential. Under normal conditions, when the inside of the cell is negative with respect to the outside, oxanol is accumulated at the outer leaflet of the membrane and excitation of coumarin will cause FRET to occur. Conditions that lead to membrane depolarization will cause the oxanol to redistribute to the inside of the cell, and, as a consequence, to a decrease in FRET. Thus, the ratio change (donor/acceptor) increases after membrane depolarization, which determines if a test compound actively blocks the maxi-K channel.

The HBEK-293 cells were obtained from the American Type Culture Collection, 12301 Parklawn Drive, Rockville, Md., 20852 under accession number ATCC CRL-1573. Any restrictions relating to public access to the microorganism shall be irrevocably removed upon patent issuance.

Transfection of the alpha and beta1 subunits of the maxi-K channel in HEK-293 cells was carried out as follows: HEK-293 cells were plated in 100 mm tissue culture treated dishes at a density of $3 \times 10^6$ cells per dish, and a total of five dishes were prepared. Cells were grown in a medium consisting of Dulbecco's Modified Eagle Medium (DMEM) supplemented with 10% Fetal Bovine serum, 1× L-Glutamine, and 1× Penicillin/Streptomycin, at 37° C., 10% $CO_2$. For transfection with Maxi-K hα(pCIneo) and Maxi-K hβ1(pIRESpuro) DNAs, 150 µl FuGENE6™ was added dropwise into 10 ml of serum free/phenol-red free DMEM and allowed to incubate at room temperature for 5 minutes. Then, the FuGENE6™ solution was added dropwise to a DNA solution containing 25 µg of each plasmid DNA, and incubated at room temperature for 30 minutes. After the incubation period, 2 ml of the FuGENE6™/DNA solution was added dropwise to each plate of cells and the cells were allowed to grow two days under the same conditions as described above. At the end of the second day, cells were put under selection media which consisted of DMEM supplemented with both 600 µg/ml G418 and 0.75 µg/ml puromycin. Cells were grown until separate colonies were formed. Five colonies were collected and transferred to a 6 well tissue culture treated dish. A total of 75 colonies were collected. Cells were allowed to grow until a confluent monolayer was obtained. Cells were then tested for the presence of maxi-K channel alpha and beta1 subunits using an assay that monitors binding of $^{125}$I-iberiotoxin-D19Y/Y36F to the channel. Cells expressing $^{125}$I-iberiotoxin-D19Y/Y36F binding activity were then evaluated in a functional assay that monitors the capability of maxi-K channels to control the membrane potential of transfected HEK-293 cells using fluorescence resonance energy transfer (FRET) ABS technology with a VIPR instrument The colony giving the largest signal to noise ratio was subjected to limiting dilution. For this, cells were resuspended at approximately 5 cells/ml, and 200 µl were plated in individual wells in a 96 well tissue culture treated plate, to add ca. one cell per well. A total of two 96 well plates were made. When a confluent monolayer was formed, the cells were transferred to 6 well tissue culture treated plates. A total of 62 wells were transferred. When a confluent monolayer was obtained, cells were tested using the FRET-functional assay. Transfected cells giving the best signal to noise ratio were identified and used in subsequent functional assays.

For functional assays:

The transfected cells (2E+06 Cells/mL) are then plated on 96-well poly-D-lysine plates at a density of about 100,000 cells/well and incubated for about 16 to about 24 hours. The medium is aspirated of the cells and the cells washed one time with 100 µl of Dulbecco's phosphate buffered saline (D-PBS). One hundred microliters of about 9 µM coumarin ($CC_2DMPE$)-0.02% pluronic-127 in D-PBS per well is added and the wells are incubated in the dark for about 30 minutes. The cells are washed two times with 100 µl of Dulbecco's phosphate-buffered saline and 100 µl of about 4.5 µM of oxanol ($DiSBAC_2(3)$) in (mM) 140 NaCl, 0.1 KCl, 2 $CaCl_2$, 1 $MgCl_2$, 20 Hepes-NaOH, pH 7.4, 10 glucose is added. Three micromolar of an inhibitor of endogenous potassium conductance of HEK-293 cells is added. A maxi-K channel blocker is added (about 0.01 micromolar to about 10 micromolar) and the cells are incubated at room temperature in the dark for about 30 minutes.

The plates are loaded into a voltage/ion probe reader (VIPR) instrument, and the fluorescence emission of both $CC_2DMPE$ and $DiSBAC_2(3)$ are recorded for 10 sec. At this point, 100 µl of high-potassium solution (mM): 140 KCl, 2 $CaCl_2$, 1 $MgCl_2$, 20 Hepes-KOH, pH 7.4, 10 glucose are added and the fluorescence emission of both dyes recorded for an additional 10 sec. The ratio $CC_2DMPE/DiSBAC_2(3)$, before addition of high-potassium solution equals 1. In the absence of maxi-K channel inhibitor, the ratio after addition of high-potassium solution varies between 1.65-2.0. When the Maxi-K channel has been completely inhibited by either a known standard or test compound, this ratio remains at 1. It is possible, therefore, to titrate the activity of a Maxi-K channel inhibitor by monitoring the concentration-dependent change in the fluorescence ratio.

The compounds of this invention were found to cause concentration-dependent inhibition of the fluorescence ratio with $IC_{50}$'s in the range of about 1 nM to about 20 µM, more preferably from about 10 nM to about 500 nM.

B. Electrophysiological Assays of Compound Effects on High-Conductance Calcium-Activated Potassium Channels Methods:

Patch clamp recordings of currents flowing through large-conductance calcium-activated potassium (maxi-K) channels were made from membrane patches excised from CHO cells constitutively expressing the α-subunit of the maxi-K channel or HEK293 cells constitutively expressing both α- and β-subunits using conventional techniques (Hamill et al., 1981, Pflügers Archiv. 391, 85-100) at room temperature. Glass capillary tubing (Garner #7052 or Drummond custom borosilicate glass 1-014-1320) was pulled in two stages to yield micropipettes with tip diameters of approximately 1-2 microns. Pipettes were typically filled with solutions containing (mM): 150 KCl, 10 Hepes (4-(2-hydroxyethyl)-1-piperazine methanesulfonic acid), 1 Mg, 0.01 Ca, and adjusted to pH 7.20 with KOH. After forming a high resistance (>$10^9$ ohms) seal between the plasma membrane and the pipette, the pipette was withdrawn from the cell, forming an excised inside-out membrane patch. The patch was excised into a bath solution containing (mM): 150 KCl, 10 Hepes, 5 EGTA (ethylene glycol bis(β-aminoethyl ether)-N,N,N',N'-tetraacetic acid), sufficient Ca to yield a free Ca concentration of 1-5 µM, and the pH was adjusted to 7.2 with KOH. For example, 4.193 mM Ca was added to give a free concentration of 1 µM at 22° C. An EPC9 amplifier (HEKA Elektronic, Lambrect, Germany) was used to control the voltage and to measure the currents flowing across the membrane patch. The input to the headstage was connected to the pipette solution with a Ag/AgCl wire, and the amplifier ground was connected to the bath solution with a Ag/AgCl wire covered with a tube filled with agar dissolved in 0.2 M KCl. The identity of maxi-K currents was confirmed by the sensitivity of channel open probability to membrane potential and intracellular calcium concentration.

Data acquisition was controlled by PULSE software (HEKA Elektronic) and stored on the hard drive of a Macintosh computer (Apple Computers) for later analysis using PULSEFIT (HEKA Elektronic) and Igor (Wavemetrics, Oswego, Oreg.) software.

Results:

The effects of the compounds of the present invention on maxi-K channels was examined in excised inside-out membrane patches with constant superfusion of bath solution. The membrane potential was held at −80 mV and brief (100-200 ms) voltage steps to positive membrane potentials (typically +50 mV) were applied once per 15 seconds to transiently open maxi-K channels. As a positive control in each experiment, maxi-K currents were eliminated at pulse potentials after the patch was transiently exposed to a low concentration of calcium (<10 nM) made by adding 1 mM EGTA to the standard bath solution with no added calcium. The fraction of channels blocked in each experiment was calculated from the reduction in peak current caused by application of the specified compound to the internal side of the membrane patch. Compound was applied until a steady state level of block was achieved. $K_I$ values for channel block were calculated by fitting the fractional block obtained at each compound concentration with a Hill equation. The $K_I$ values for channel block by the compounds described in the present invention range from 0.01 nM to greater than 10 µM.

What is claimed is:
1. A compound of the structural formula I:

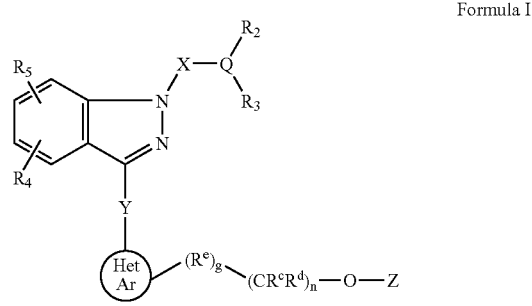

Formula I or a pharmaceutically acceptable salt, in vivo hydrolysable ester, enantiomer, diastereomer or mixture thereof: wherein, R represents hydrogen, or $C_{1-6}$ alkyl;
$R^c$ and $R^d$ independently represents hydrogen or halo;
$R^e$ represents N or O;
X represents —$(CHR_7)_p$—, —$(CHR_7)_pCO$—;
Y represents —$CO(CH_2)_n$—, $CH_2$, or —CH(OR)—;
Q represents N, or O, wherein $R_2$ is absent when Q is O;
$R_w$ represents H, $C_{1-6}$ alkyl, —$C(O)C_{1-6}$ alkyl, —$C(O)OC_{1-6}$ alkyl, —$SO_2N(R)_2$, —$SO_2C_{1-6}$ alkyl, —$SO_2C_{6-10}$ aryl, $NO_2$, CN or —$C(O)N(R)_2$;
$R_2$ represents hydrogen, $C_{1-10}$ alkyl, OH, $C_{2-6}$ alkenyl, $C_{1-6}$ alkylSR, —$(CH_2)_nO(CH_2)_mOR$, —$(CH_2)_nC_{1-6}$ alkoxy, —$(CH_2)_nC_{3-8}$ cycloalkyl, —$(CH_2)_nC_{3-10}$ heterocyclyl, —$N(R)_2$, —COOR, or —$(CH_2)_nC_{6-10}$ aryl, said alkyl, heterocyclyl, or aryl optionally substituted with 1-3 groups selected from $R^a$;
$R_3$ represents hydrogen, $C_{1-10}$ alkyl, —$(CH_2)_nC_{3-8}$ cycloalkyl, —$(CH_2)_nC_{3-10}$ heterocyclyl, —$(CH_2)_n$COOR, —$(CH_2)_nC_{6-10}$ aryl, —$(CH_2)_nNHR_8$, —$(CH_2)_nN(R)_2$, —$(CH_2)_nN(R_8)_2$, —$(CH_2)_n$NHCOOR, —$(CH_2)_n N(R_8)CO_2R$, —$(CH_2)_nN(R_8)COR$, —$(CH_2)_n$NHCOR, —$(CH_2)_nCONH(R_8)$, aryl, —$(CH_2)_nC_{1-6}$ alkoxy, $CF_3$, —$(CH_2)_nSO_2R$, —$(CH_2)_nSO_2N(R)_2$, —$(CH_2)_nCON(R)_2$, —$(CH_2)_nCONHC(R)_3$, —$(CH_2)_n$CONHC$(R)_2CO_2R$, —$(CH_2)_nCOR_8$, nitro, cyano or halogen, said alkyl, alkoxy, heterocyclyl, or aryl optionally substituted with 1-3 groups of $R^a$;
or, $R_2$ and $R_3$ taken together with the intervening Q form a 3-10 membered carbocyclic or heterocyclic carbon ring optionally interrupted by 1-2 atoms of O, S, C(O) or NR, and optionally having 1-4 double bonds, and optionally substituted by 1-3 groups selected from $R^a$;
$R_4$ and $R_5$ independently represent hydrogen, $C_{1-6}$ alkoxy, OH, $C_{1-6}$ alkyl, COOR, $SO_3H$, —$O(CH_2)_nN(R)_2$, —$O(CH_2)_nCO_2R$, —$OPO(OH)_2$, $CF_3$, $OCF_3$, —$N(R)_2$, nitro, cyano, $C_{1-6}$ alkylamino, or halogen;

represents phenyl, napthyl, phenanthrenyl, pyridyl, said phenyl, napthyl, phenanthrenyl, pyridyl optionally substituted with 1-3 groups selected from $R^a$;
Z represents $(CH_2)_nPO(OR)(OR^*)$;
$R^*$ represents hydrogen, or $C_{1-6}$ alkyl;
$R_7$ represents hydrogen, $C_{1-6}$ alkyl, —$(CH_2)_n$COOR or —$(CH_2)_nN(R)_2$,
$R_8$ represents —$(CH_2)_nC_{3-8}$ cycloalkyl, —$(CH_2)_n$ 3-10 heterocyclyl, $C_{1-6}$ alkoxy or —$(CH_2)_nC_{5-10}$ heteroaryl, —$(CH_2)_nC_{6-10}$ aryl said heterocyclyl, aryl or heteroaryl optionally substituted with 1-3 groups selected from $R^a$;
$R^a$ represents F, Cl, Br, I, $CF_3$, $N(R)_2$, $NO_2$, CN, —$COR_8$, —$CONHR_8$, —$CON(R_8)_2$, —$O(CH_2)_n$COOR, —NH$(CH_2)_n$OR, —COOR, —$OCF_3$, —NHCOR, —$SO_2R$, —$SO_2NR_2$, —SR, ($C_1$-$C_6$ alkyl)O—, —$(CH_2)_nO(CH_2)_m$ OR, —$(CH_2)_nC_{1-6}$ alkoxy, (aryl)O—, —$(CH_2)_n$OH, ($C_1$-$C_6$ alkyl)S(O)$_m$—, $H_2N$—C(NH)—, ($C_1$-$C_6$ alkyl)C(O)—, ($C_1$-$C_6$ alkyl)OC(O)NH—, —($C_1$-$C_6$ alkyl)NR$_w$(CH$_2$)$_n$C$_{3-10}$ heterocyclyl-R$_w$, —($C_1$-$C_6$ alkyl)O(CH$_2$)$_n$C$_{3-10}$ heterocyclyl-R$_w$, —($C_1$-$C_6$ alkyl)S (CH$_2$)$_n$ C$_{3-10}$ heterocyclyl-R$_w$, —($C_1$-$C_6$ alkyl)-C$_{3-10}$ heterocyclyl-R$_w$, —$(CH_2)_n$-$Z^1$-C(=$Z^2$)N(R)$_2$, —(C$_{2-6}$ alkenyl)NR$_w$(CH$_2$)$_n$C$_{3-10}$ heterocyclyl-R$_w$, —(C$_{2-6}$ alkenyl)O(CH$_2$)$_n$C$_{3-10}$ heterocyclyl-R$_w$, —(C$_{2-6}$ alkenyl)S (CH$_2$)$_n$C$_{3-10}$ heterocyclyl-R$_w$, —(C$_{2-6}$ alkenyl)-C$_{3-10}$ heterocyclyl-R$_w$, —(C$_{2-6}$ alkenyl)-$Z^1$-C(=$Z^2$)N(R)$_2$, —(CH$_2$)$_n$SO$_2$R, —(CH$_2$)$_n$SO$_3$H, —(CH$_2$)$_n$PO(OR)$_2$, C$_{3-10}$cycloalkyl, C$_{6-10}$aryl, C$_{3-10}$heterocyclyl, C$_{2-6}$alkenyl, and C$_1$-C$_{10}$alkyl, said alkyl, alkenyl, alkoxy, heterocyclyl and aryl optionally substituted with 1-3 groups selected from C$_1$-C$_6$ alkyl, CN, NO$_2$, OH, CON(R)$_2$ and COOR;

Z$^1$ and Z$^2$ independently represents NR$_w$, O, CH$_2$, or S;

g is 0-1;

m is 0-3;

n is 0-3; and p is 0-3.

2. The compound according claim 1 wherein p is 1-3, Y is —CO(CH$_2$)$_n$—, Q is N, X is —(CHR$_7$)$_p$—, or —(CHR$_7$)$_p$CO—.

3. The compound according claim 1 wherein Q is O and R$_2$ is absent.

4. The compound according to claim 2 wherein Z is PO(OR)(OR*), R$_2$ is C$_{1-10}$ alkyl or C$_{1-6}$ alkylOH, Y is —CO(CH$_2$)$_n$ and R$_3$ is (CH$_2$)$_n$C$_{3-10}$ heterocyclyl, said heterocyclyl and alkyl optionally substituted with 1 to 3 groups of R$^a$.

5. The compound according to claim 4 wherein

is a pyridyl or phenyl optionally substituted with 1-3 groups selected from R$^a$.

6. A compound according to claim 1 wherein

is pyridyl optionally substituted with 1-3 groups selected from R$^a$.

7. A compound according to claim 1 which is in the form of a sodium or disodium salt.

8. A compound which is:

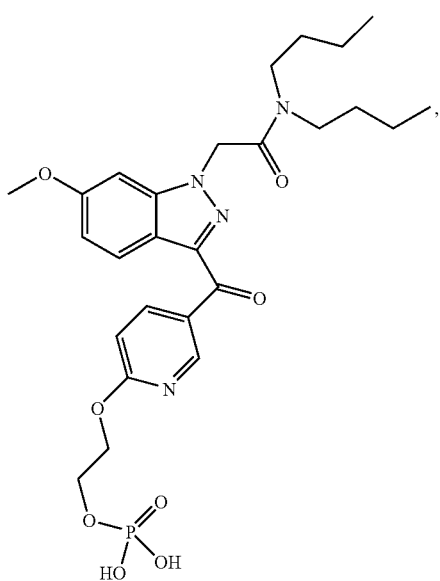

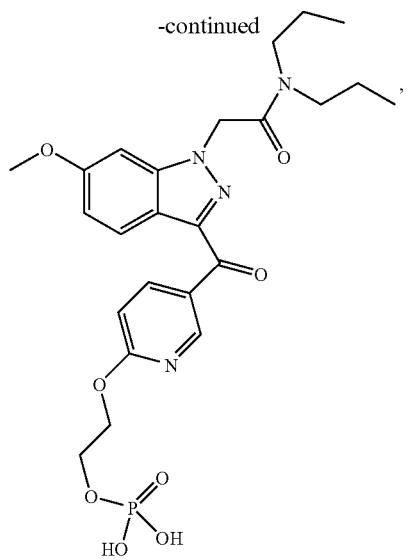

-continued

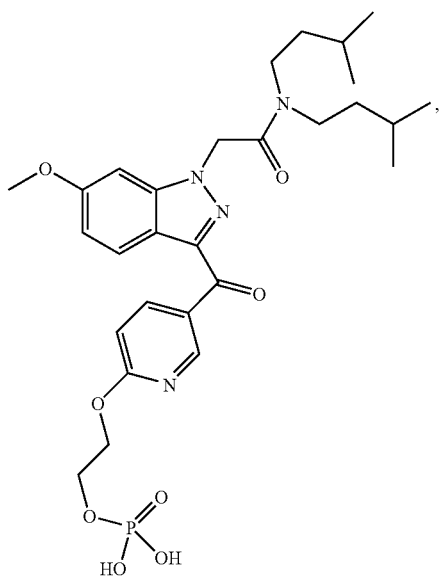

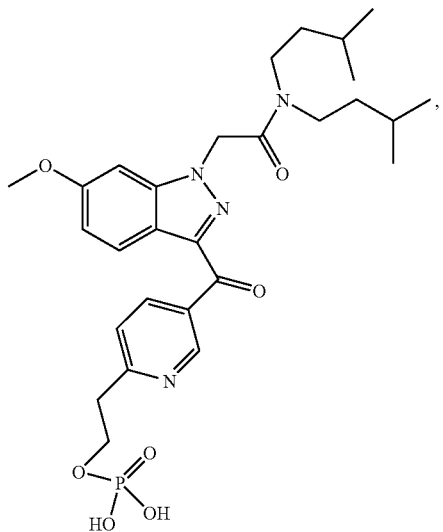

-continued

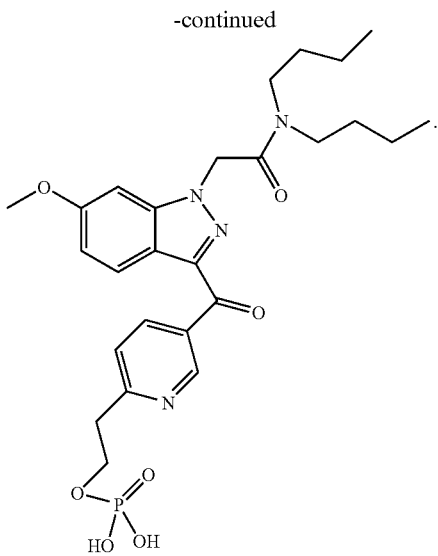

or a pharmaceutically acceptable salt, in vivo hydrolysable ester, enantiomer, diastereomer or mixture thereof.

9. A method for the treatment of ocular hypertension or glaucoma comprising administering a compound of formula I accordingly to claim 1.

10. A method for the treatment of macular edema, macular degeneration, increasing retinal and optic nerve head blood velocity, increasing retinal and optic nerve oxygen tension, and/or a neuroprotective effect comprising administering a compound of formula I accordingly to claim 1.

11. A composition comprising a compound of formula I of claim 1 and a pharmaceutically acceptable carrier.

12. The composition according to claim 11 wherein the compound of formula I is applied as a topical formulation, said topical formulation administered as a solution or suspension and optionally containing xanthan gum or gellan gum.

13. A composition according to claim 12 wherein one or more of an active ingredient belonging to the group consisting of: β-adrenergic blocking agent, parasympatho-mimetic agent, sympathomimetic agent, carbonic anhydrase inhibitor, EP4 agonist, a prostaglandin, hypotensive lipid, neuroprotectant, and/or 5-HT2 receptor agonist is optionally added.

14. A composition according to claim 13 wherein the β-adrenergic blocking agent is timolol, betaxolol, levobetaxolol, carteolol, or levobunolol; the parasympathomimetic agent is pilocarpine; the sympathomimetic agent is epinephrine, brimonidine, iopidine, clonidine, or para-aminoclonidine, the carbonic anhydrase inhibitor is dorzolamide, acetazolamide, metazolamide or brinzolamide; the prostaglandin is latanoprost, travaprost, unoprostone, rescula, or S1033, the hypotensive lipid is lumigan, the neuroprotectant is eliprodil, R-eliprodil or memantine; and the 5-HT2 receptor agonist is 1-(2-aminopropyl)-3-methyl-1H-imdazol-6-ol fumarate or 2-(3-chloro-6-methoxy-indazol-1-yl)-1-methyl-ethylamine.

* * * * *